US008871198B2

(12) United States Patent
Emig et al.

(10) Patent No.: US 8,871,198 B2
(45) Date of Patent: *Oct. 28, 2014

(54) METHODS RELATED TO WOUND HEALING

(75) Inventors: Charlotte A Emig, Gibsonia, PA (US); Catherine J Trumpower, Pittsburgh, PA (US); Vivienne S Marshall, San Antonio, TX (US)

(73) Assignee: Stemnion, Inc., Pittsburgh, PA (US)

( * ) Notice: Subject to any disclaimer, the term of this patent is extended or adjusted under 35 U.S.C. 154(b) by 1709 days.

This patent is subject to a terminal disclaimer.

(21) Appl. No.: 11/724,094

(22) Filed: Mar. 14, 2007

(65) Prior Publication Data

US 2007/0231297 A1 Oct. 4, 2007

Related U.S. Application Data

(63) Continuation-in-part of application No. 11/392,892, filed on Mar. 29, 2006, which is a continuation-in-part of application No. 11/333,849, filed on Jan. 18, 2006.

(60) Provisional application No. 60/666,949, filed on Mar. 31, 2005, provisional application No. 60/699,257, filed on Jul. 14, 2005, provisional application No. 60/742,067, filed on Dec. 2, 2005.

(51) Int. Cl.
| | | |
|---|---|---|
| *A01N 63/00* | (2006.01) | |
| *C12N 5/073* | (2010.01) | |
| *A61K 35/50* | (2006.01) | |
| *C12N 5/071* | (2010.01) | |
| *A61K 35/12* | (2006.01) | |

(52) U.S. Cl.
CPC ............ *A61K 35/50* (2013.01); *C12N 2501/11* (2013.01); *C12N 5/0605* (2013.01); *C12N 5/0629* (2013.01); *A61K 35/12* (2013.01); *C12N 2502/02* (2013.01)
USPC ........... 424/93.7; 435/325; 435/363; 435/366

(58) Field of Classification Search
CPC ... A61K 35/50; A61K 2300/00; A61K 38/00; A61K 35/36; A61K 35/28; C12N 5/0605; A61Q 19/00; A61M 35/00
See application file for complete search history.

(56) References Cited

U.S. PATENT DOCUMENTS

| | | | | |
|---|---|---|---|---|
| 4,361,552 | A | | 11/1982 | Baur, Jr. |
| 4,474,181 | A | * | 10/1984 | Schenck ........................ 606/155 |
| 5,217,951 | A | * | 6/1993 | Lezdey et al. ..................... 514/8 |
| 5,597,808 | A | * | 1/1997 | Haimes et al. .................. 514/33 |
| 7,045,148 | B2 | | 5/2006 | Hariri |
| 7,560,276 | B2 | * | 7/2009 | Harmon et al. ............... 435/325 |
| 2003/0032179 | A1 | | 2/2003 | Hariri |
| 2003/0235563 | A1 | | 12/2003 | Strom |
| 2003/0235580 | A1 | | 12/2003 | Zhang |
| 2004/0048372 | A1 | | 3/2004 | Hariri |
| 2004/0057938 | A1 | | 3/2004 | Ghinelli |
| 2004/0161419 | A1 | | 8/2004 | Strom |
| 2004/0170615 | A1 | | 9/2004 | Soo |
| 2005/0124003 | A1 | | 6/2005 | Atala |
| 2006/0078993 | A1 | | 4/2006 | Phan |
| 2006/0222634 | A1 | | 10/2006 | Clarke |
| 2007/0031508 | A1 | * | 2/2007 | Armstrong et al. ........... 424/572 |

FOREIGN PATENT DOCUMENTS

| | | | | |
|---|---|---|---|---|
| GB | 2110531 | A * | 6/1983 | ............. A61K 35/50 |
| WO | PCT/US00/40052 | | 6/2000 | |
| WO | PCTSG05/000174 | | 6/2005 | |

OTHER PUBLICATIONS

Kamiya K et al. 2005. Topical application of culture supernatant from human amniotic epithelial cells suppresses inflammatory reactions in cornea. Exp Eye Res 80: 671-679.*
Levin MH et al. 2004. Aquaporin-dependent water permeation at the mouse ocular surface: in vivo microfluorimetric measurements in cornea and conjunctiva . . . Invest Ophthalmol Vis Sci 45: 4423-4432.*
Robson, M.C. and Krizek, T.J. (1973) The effect of human amniotic membranes on the bacterial population of infected rat burns. Ann of Surg, 177:144-149.
Robson, M.C., et al., (1973) Quantitative comparison of biological dressings. Jour Surg Res 14:431-434.
Robson, M.C., et al., (1973) Amniotic membranes as a temporary wound dressing. Surgery, Ob & Gyn, 136:904-906.
Robson, M.C. and Krizek, T. J., (1974) Clinical experiences with amniotic membranes as a temporary biologic dressing. Connecticut Med 38:449-451.
Kucan, J.O., et al, (1982) Amniotic membranes as dressings following facial dermabrasion. Ann Plast Surg 8:523-527.
Wu, C-H, et al., (2003) Wound healing effects of porcine placental extracts on rats with thermal injury. British J Dermatol 148:236-245.
Koyano et al., (2002) Synthesis and release of activin and noggin by cultured human amniotic epithelial cells. Develop. Growth Differ. 44:103-112.
Tahara et al. (1995) Expression of messenger ribonucleic acid . . . J. Clin. Endocrinol. Metabol. 80:138-146.
Denison et al. (1998) Cytokine secretion by human fetal membranes, decidua and placenta at term. Hum. Reprod. 13:3560-3565.
Uchida et al. (2000) Neurotrophic function of conditioned medium from human amniotic epithelial cells. J. Neurosci. Res. 62:585-590.
Sun et al. (2003) Glucocorticoids induce cytosolic . . . J.Clin. Endocrinol. Metabol. 88(11):5564-5571.
Marvin et al. (2002) Expression of angiogenic and neurotrophic factors in the human amnion and choriodecidua. Am. J. Obstet. Gynecol. 187(3):728-734.
Ihara et al, (1992) Wound closure in foetal rat skin. Development 114: 573-82.
Ladwig, et al. (2002) Ratios of activated matrix metalloproteinase-9 to tissue inhibitor . . . Wound Rep Reg 10:26-37.
Parolina, Ornella, et al., Stem Cells 2008;26:300-311.

* cited by examiner

*Primary Examiner* — Lora E Barnhart Driscoll
(74) *Attorney, Agent, or Firm* — Linda O. Palladino; Gail M. Kempler

(57) ABSTRACT

The invention is directed to methods for the treatment of wounds. Such methods utilize novel compositions, including but not limited to amnion-derived multipotent cells (herein referred to as AMP cells), conditioned media derived therefrom (herein referred to as amnion-derived cellular cytokine suspension or ACCS), cell lysates derived therefrom, cell products derived therefrom, each alone or in combination.

7 Claims, No Drawings

METHODS RELATED TO WOUND HEALING

CROSS-REFERENCE TO RELATED APPLICATIONS

This application claims priority under 35 USC §119(e) to U.S. Provisional Application No. 60/666,949, filed Mar. 31, 2005, U.S. Provisional Application No. 60/699,257, filed Jul. 14, 2005, U.S. Provisional Application No. 60/742,067, filed Dec. 2, 2005, and under 35 USC §120 to U.S. Utility application Ser. No. 11/333,849, filed Jan. 18, 2006 (now abandoned), and U.S. Utility application Ser. No. 11/392,892, filed Mar. 29, 2006, the contents of which are incorporated herein by reference in their entirety.

STATEMENT REGARDING FEDERALLY SPONSORED RESEARCH OR DEVELOPMENT

This invention was made in part with United States government support awarded by the following agency: U.S. Army Medical Research Acquisition Activity, ERMS #06100002 and #06153010. The United States may have certain rights to this invention.

FIELD OF THE INVENTION

The field of the invention is directed to methods for the treatment of wounds. Such methods utilize novel compositions, including but not limited to extraembryonic cytokine secreting cells (herein referred to as ECS cells), including, but not limited to, amnion-derived multipotent cells (herein referred to as AMP cells), conditioned media derived therefrom (herein referred to as amnion-derived cellular cytokine suspension or ACCS), cell lysates derived therefrom, and cell products derived therefrom, each alone or in combination.

DESCRIPTION OF RELATED ART

Amniotic membranes have been used clinically as wound dressing for burn patients for over 100 years to promote epithelialization, reduce pain, and prevent infection (Robson, M. C. and Krizek, T. J. (1973) Ann of Surg, 177:144-149; Robson, M. C., et al., (1973) Jour Surg Res 14:431-434; Robson, M. C., et al., (1973) Surgery, Ob & Gyn, 136:904-906; Robson, M. C. and Krizek, T. J., (1974) Connecticut Med 38:449-451; Krizek, T. J. and Robson, M. C., A rebirth of amniotic membranes, in Marchac (Ed): Transactions of VI International Congress of Plastic and Reconstructive Surgery, Masson, Inc., NY, 1976; Kucan, J. O., et al, (1982) Ann Plast Surg 8:523-527; Wu, C-H, et al., (2003) British J Dermatol 148:236-245; Bose, B. (1979) Ann R Coll Surg Engl, 61:444-7; Sawhney, C. P. (1989) Burns, 15:339-42, Thomson, P. D., Parks, D. H. (1981) Ann Plast Surg, 7:354-6). US2003/0235580 describes a method of delivering therapeutic molecules to skin using amniotic epithelial cells. US2004/0057938 describes the use of a human amniotic membrane composition for prophylaxis and treatment of diseases and conditions of the eye and skin. U.S. Pat. No. 4,361,552 describes a method of treating a wound or burn, which comprises covering the surface of the wound or burn with a cross-linked amnion dressing. US2004/0170615 describes the use of compounds expressed in fetal tissue for use in skin repair and the improvement of skin appearance.

BACKGROUND OF THE INVENTION

Placental tissue is abundantly available as a discarded source of many potentially useful cell types including a type of multipotent cell called placental-derived cells. Although discarded at parturition as part of the placental membranes, lineage analysis shows that, the epithelial layer of the amnion, from which such multipotent cells can be isolated, is uniquely descended from the epiblast in embryonic development. The epiblast contains the cells that will ultimately differentiate into the embryo and cells that will give rise to an extraembryonic tissue, the amnion. Thus far, only four cell types have been described in the literature as being pluripotent. These are the inner cell mass (ICM) of the pre-implantation embryo, which gives rise to the epiblast, the epiblast itself, embryonic stem (ES) and embryonic germ cells (EG). Thus, identification, purification and propagation of a multipotent cell population from discarded amnion tissue would provide an extremely valuable source of stem cells for replacement cell therapy.

With an average yield of over 200 million cells per placenta, large numbers of cells are available from this source. If these cells were to become useful cells for transplantation medicine, they could provide a nearly inexhaustible supply of starting material in every part of the world. No stem cell source provides such a large starting population of cells, and collection does not require an invasive or destructive procedure. Furthermore, there are no ethical, religious or social issues associated with these cells as the tissue is derived from the placenta.

Another important consideration in stem cell therapies is immune tolerance. In humans, the protein expression of the cell surface marker HLA-G was originally thought to be restricted to immune-privileged sites such as placenta, as well as related cells, including some isolated from amniotic fluid, placental macrophages, and cord blood, thus implicating its role in maternal-fetal tolerance (Urosevic, M. and Dummer, R. (2002) ASHI Quarterly; 3rd Quarter 2002:106-109). Additionally, studies involving heart-graft acceptance have suggested that the protein expression of HLA-G may enhance graft tolerance (Lila, N., et al. (2000) Lancet 355:2138; Lila, N. et al. (2002) Circulation 105:1949-1954). HLA-G protein is not expressed on the surface of undifferentiated or differentiated embryonic stem cells (Drukker, M, et al. (2002) PNAS 99(15):9864-9869). Thus, it is desirable that stems cells intended for cell-based therapies express HLA-G protein.

Placental-derived cells have been shown to secrete many cytokines and growth factors including prostaglandin E2, PGES, TGF-β, EGF, IL-4, IL-8, TNF, interferons, activin A, noggin, bFGF, some neuroprotective factors, and many angiogenic factors (Koyano et al., (2002) Develop. Growth Differ. 44:103-112; Blumenstein et al. (2000) Placenta 21:210-217; Tahara et al. (1995) J. Clin. Endocrinol. Metabol. 80:138-146; Paradowska et al. (1997) Placenta 12:441-446; Denison et al. (1998) Hum. Reprod. 13:3560-3565; Keelan et al. (1998) Placenta 19:429-434; Uchida et al. (2000) J. Neurosci. Res. 62:585-590; Sun et al. (2003) J. Clin. Endocrinol. Metabol. 88(11):5564-5571; Marvin et al. (2002) Am. J. Obstet. Gynecol. 187(3):728-734). Many of these cytokines are associated with wound healing and some have been credited with contributing to scarless healing in the fetus. Fetal skin has much more effective repair mechanisms than adult skin and, once wounded, it is able to heal without the formation of scars. This capability does appear to require the fetal immune system, fetal serum, or amniotic fluid (Bleacher J C, et al., J Pediatr Surg 28: 1312-4, 1993); Ihara S, Motobayashi Y., Development 114: 573-82. 1992). Such abilities of fetal tissue have led to the suggested use of compounds produced by fetal tissue for regenerating and/or improving the appearance of skin (see, for example, US 2004/0170615, which is incorporated by reference in its entirety herein).

Approximately 50 million surgical procedures are performed in the United States each year. An additional 50 million wounds result from traumatic injuries. Subsequent acute wound healing failure at any anatomic site results in increased morbidity and mortality. Non-limiting examples of acute wound failure include muscle, fascial and skin dehiscence, incisional hernia formation, gastrointestinal fistulization and vascular anastamotic leaks. Besides the immediate functional disability, acute wounds that fail usually go on to form disabling scars.

Incisional hernias of the abdominal wall provide an excellent paradigm to study the mechanism and outcome of acute wound healing failure. Large, prospective, well-controlled studies have shown that 11-20% of over 4 million abdominal wall fascial closures fail leading to ventral incisional hernia formation. Even after repair of acute wound failure, recurrence rates remain as high as 58%. Improvements in suture material, stitch interval, stitch distance from the margin of the wound, and administration of prophylactic antibiotics to avoid infection significantly decreased the rates of clinically obvious acute wound dehiscence, but only led to small decreases in the rates of ventral hernia formation and recurrence. The introduction of tissue prostheses, typically synthetic meshes, to create a tension-free bridge or patch of the myo-fascial defect reduced first recurrence rates significantly, supporting the concept that mechanical factors predominate in the pathogenesis of recurrent hernia.

Traditional surgical teaching is that laparotomy wound failure is a rare event, with reported "fascial dehiscence" rates clustered around 0.1%. One prospective study found that the true rate of laparotomy wound failure is closer to 11%, and that the majority of these (94%) go on to form incisional hernias during the first three years after abdominal operations. This is more in line with the high incidence of incisional hernia formation. The real laparotomy wound failure rate is therefore 100 times what most surgeons think it is. In simplest terms, most incisional hernias are derived from clinically occult laparotomy wound failures, or occult fascial dehiscences. The overlying skin wound heals, concealing the underlying myofascial defect. This mechanism of early mechanical laparotomy wound failure is more consistent with modern acute wound healing science.

BRIEF SUMMARY OF THE INVENTION

It is an object of the instant invention to provide novel methods for the treatment of wounds. Such methods utilize novel compositions including extraembryonic cytokine secreting cells (herein referred to as ECS cells), conditioned media derived therefrom, cell lysates derived therefrom, and cell products derived therefrom, each alone and/or in combination with each other and/or with other agents including active and/or inactive agents. In a particular preferred embodiment, the methods utilize novel compositions including, but not limited to, amnion-derived multipotent cells (herein referred to as AMP cells), conditioned media derived therefrom (herein referred to as amnion-derived cellular cytokine suspension or ACCS), cell lysates derived therefrom, and cell products derived therefrom, each alone and/or in combination with each other and/or with other agents including active and/or inactive agents. In a most preferred embodiment, wounds are treated with ACCS, including pooled ACCS.

It is also an object of the instant invention to promote accelerated wound healing using the novel compositions described herein. It is further an object of the invention to reduce or prevent scarring following wound healing; to promote the formation of stronger healed wounds by increasing tensile strength and/or breaking strength; and to prevent or reduce wound healing failure, in particular, hernia formation, using the novel compositions described herein.

Accordingly, a first aspect of the invention is a method for promoting accelerated wound healing in a patient in need thereof comprising administering to the patient a therapeutically effective amount of one or more compositions comprising ECS cells, conditioned media derived therefrom, cell lysate derived therefrom or cell products derived therefrom. In one embodiment the ECS cells are AMP cells. In a preferred embodiment the AMP cells are pooled AMP cells. In another embodiment the conditioned media is ACCS. In a preferred embodiment the ACCS is pooled ACCS. In yet another embodiment the cell lysates are AMP cell lysates. In a preferred embodiment the AMP cell lysates are pooled AMP cell lysates. In yet another embodiment the cell products are AMP cell products. In a preferred embodiment the AMP cell products are pooled AMP cell products. In still another embodiment the patient is a human patient.

A second aspect of the invention is a method for decreasing wound failure in a surgical patient in need thereof comprising administering to the patient a therapeutically effective amount of one or more compositions comprising ECS cells, conditioned media derived therefrom, cell lysate derived therefrom or cell products derived therefrom.

A third aspect of the invention is a method for increasing tensile strength and breaking strength of a wound in a patient in need thereof comprising administering to the patient a therapeutically effective amount of one or more compositions comprising ECS cells, conditioned media derived therefrom, cell lysate derived therefrom or cell products derived therefrom.

In one embodiment of aspects one, two and three of the invention the ECS cells are AMP cells. In a preferred embodiment the AMP cells are pooled AMP cells. In another embodiment the conditioned media is ACCS. In a preferred embodiment the ACCS is pooled ACCS. In yet another embodiment the cell lysates are AMP cell lysates and in a preferred embodiment the AMP cell lysates are pooled AMP cell lysates. In yet another embodiment the cell products are AMP cell products and in a preferred embodiment the AMP cell products are pooled AMP cell products. In still another embodiment the patient is a human patient.

In other embodiments the wound is a congenital wound or an acquired wound. In preferred embodiments the congenital wound is epidermolysis or scalp aplasia. In other preferred embodiments the acquired wound is an acute wound or a chronic wound. In still other preferred embodiments the acute wound is trauma or a surgical incision and the trauma wound is a burn, open fracture or avulsion. In still other preferred embodiments the chronic wound is a pressure ulcer, venous ulcer, diabetic ulcer, sickle cell ulcer or peptic ulcer.

A fourth aspect of the invention is a method to reduce the occurrence of tissue scarring and adhesion formation during the wound healing process after surgery, which comprises applying to the surgical site a therapeutically effective amount of AMP cells and/or ACCS. In a preferred embodiment the AMP cells and ACCS are pooled AMP cells and pooled ACCS. In another preferred embodiment the applying of AMP cells and/or ACCS to the surgical site occurs prior to the surgical procedure. In another preferred embodiment the applying of AMP cells and/or ACCS to the surgical site occurs during the surgical procedure. In still another preferred embodiment the applying of AMP cells and/or ACCS to the surgical site occurs or after the surgical procedure. In other preferred embodiments, the applying of AMP cells and/or ACCS to the surgical site occurs prior to, during and after the surgical procedure. Other combinations for applying of AMP cells and/or ACCS to the surgical site are contemplated by the methods of the invention.

A fifth aspect of the invention is a method for stimulating growth or regeneration of epidermal cells and inhibiting fibrosis and collagen contraction in a patient in need thereof comprising contacting the patient's epidermal cells with a therapeutic amount of AMP cells and/or ACCS. In a preferred embodiment the AMP cells and ACCS are pooled AMP cells and pooled ACCS. In still another embodiment the patient is a human patient.

A sixth aspect of the invention is a method for preventing keloid and/or hypertrophic scar formation at the site of a wound in a patient in need thereof comprising contacting the patient's wound with an amount of AMP cells and/or ACCS sufficient to stimulate growth and regeneration of epidermal cells and inhibit fibrosis and collagen contraction. In a preferred embodiment the AMP cells and ACCS are pooled AMP cells and pooled ACCS. In still another embodiment the patient is a human patient.

A seventh aspect of the invention is a cosmetic preparation comprising one or more compositions comprising AMP cells, ACCS, AMP cell lysates or AMP cell products. In a preferred embodiment the AMP cells are pooled AMP cells. In a preferred embodiment the ACCS is pooled ACCS. In yet another the AMP cell lysates are pooled AMP cell lysates. In yet another embodiment the AMP cell products are pooled AMP cell products.

Other features and advantages of the invention will be apparent from the accompanying description, examples and the claims. The contents of all references, pending patent applications and published patents, cited throughout this application are hereby expressly incorporated by reference. In case of conflict, the present specification, including definitions, will control.

Definitions

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristic of secreting a unique combination of physiologically relevant cytokines in a physiologically relevant temporal manner into the extracellular space or into surrounding culture media. In one embodiment, the ECS cells secrete at least one cytokine selected from VEGF, Angiogenin, PDGF and TGFβ2 and at least one MMP inhibitor selected from TIMP-1 and TIMP-2. In another embodiment, the ECS cells secrete more than one cytokine selected from VEGF, Angiogenin, PDGF and TGFβ2 and more than one MMP inhibitor selected from TIMP-1 and TIMP-2. In a preferred embodiment, the ECS cells secrete the cytokines VEGF, Angiogenin, PDGF and TGFβ2 and the MMP inhibitors TIMP-1 and TIMP-2. The physiological range of the cytokine or cytokines in the unique combination is as follows: ~5-16 ng/ml for VEGF, ~3.5-4.5 ng/ml for Angiogenin, ~100-165 pg/ml for PDGF, ~2.5-2.7 ng/ml for TGFβ2, ~0.68 μg ml for TIMP-1 and ~1.04 μg/ml for TIMP-2. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. Nos. 11/333, 849, 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172: 493-500). However, the methods used herein provide improved compositions and populations of cells. AMP cells have previously been described as "amnion-derived cells" (see U.S. Provisional Application Nos. 60/666,949, 60/699, 257, 60/742,067, 60/813,759, U.S. application Ser. Nos. 11/333,849, 11/392,892, and PCTUS06/011392, each of which is incorporated herein in its entirety).

By the term "animal-free" when referring to compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "amnion-derived cellular cytokine suspension" or "ACCS" means conditioned medium that has been derived from AMP cells or expanded AMP cells.

The term "physiological level" as used herein means the level that a substance in a living system is found and that is relevant to the proper functioning of a biochemical and/or biological process.

As used herein, the term "pooled" means a plurality of compositions that have been combined to create a new composition having more constant or consistent characteristics as compared to the non-pooled compositions. For example, pooled AMP cells have more constant or consistent characteristics compared to non-pooled AMP cells.

The term "therapeutically effective amount" means that amount of a therapeutic agent necessary to achieve a desired physiological effect (i.e. accelerated wound healing).

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

As used herein, the term "pharmaceutically acceptable" means that the components, in addition to the therapeutic agent, comprising the formulation, are suitable for administration to the patient being treated in accordance with the present invention.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein "germ cells" means embryonic germ cells, adult germ cells and the cells that they give rise to (i.e. oocyte and sperm).

The term "transplantation" as used herein refers to the administration of a composition comprising cells that are either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical, thermal, and incisional injuries; elective injuries such as surgery and resultant incisional hernias; acute wounds, chronic wounds, infected wounds, and sterile wounds, as well as wounds associated with disease states (i.e. ulcers caused by diabetic neuropathy). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances such that healing is faster, and/or the resulting healed area has less scaring and/or the wounded area possesses tissue tensile strength that is closer to that of uninjured tissue.

As used herein, the term "cosmeceutical" means cosmetic products that may have drug-like benefits. Examples of products typically labeled as cosmeceuticals include anti-aging creams and moisturizers. Cosmeceuticals may contain potentially active ingredients such as vitamins, phytochemicals, enzymes, antioxidants, and essential oils.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that stated range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses

Wound healing—The instant invention is based upon the discovery that undifferentiated, partially differentiated or fully differentiated ECS cells, and in particular, AMP cells, ACCS derived therefrom, cell lysates therefrom, cell products derived therefrom, and extracellular matrices therefrom, alone or in combination with each other and/or other agents, including active and non-active agents, as well as compositions of ECS cells as defined herein, can accelerate the wound healing process for all wound types, particularly when administered topically, i.e. to the surface of the wound site, or subcutaneously. Using ECS cells, and in particular, AMP cells and preferably ACCS derived from AMP cells, all wound types, mechanical or thermal, acute or chronic, infected or sterile, or congenital, undergo healing more rapidly than similar wounds left to heal naturally or which are treated with currently available methods.

The compositions and methods of the present invention are effective in accelerating wound healing of wounds caused by a number of sources, including but not limited to incisional, compression, thermal, acute, chronic, infected, sterile and congenital injuries.

In addition to accelerating wound healing, the compositions of the invention prevent and/or reduce the incidence of wound failure, such as hernia formation, by increasing both breaking strength and tensile strength of wounds as well as increasing the rate in which increased breaking strength and tensile strength is attained during the wound healing process. Thus, wounds not only heal faster, but become stronger faster than wounds treated with other available agents or untreated.

Importantly, it has been discovered that the AMP cells and ACCS of the invention are able to accelerate the rate of wound healing (including increased wound strength) in both non-contaminated and contaminated (infected) wounds. It is long known in the art that infected wounds either do not heal or the rate of healing is very slow. However, using the novel compositions and methods described herein, Applicants have found that the rate of wound healing is accelerated even when the wound is infected. This unique ability to heal the wounds in the face of infection is not based on any antibacterial effect of the compositions, but rather is due to the unique combination of physiologically relevant cytokines secreted by the cells of the invention at physiological levels. The secretion of these physiologically relevant cytokines may be into the extracellular space in which they are placed or into culture media to form ACCS. Such physiologically relevant cytokines include VEGF, PDGF, Angiogenin, TGFβ2, TIMP-1 and TIMP-2. Because the effectiveness of the AMP cell and in particular the ACCS compositions are due to this unique cytokine profile, it is believed that any ECS composition that produces a comparable cytokine profile will be equally effective and is thus contemplated by the instant invention.

These cytokines are known to be involved in many physiological processes including wound healing. VEGF and Angiogenin are both involved in regulating angiogenesis and vascularization. PDGF is involved in regulating cell growth and division and, like VEGF and Angiogenin, plays a significant role in angiogenesis. TGFβ2 is a member of the TGF superfamily, a group of cytokines that play a number of different roles in many cellular functions. TIMP-1 and TIMP-2 are tissue inhibitors of metalloproteinases (MMPs). MMPs are a family of inflammatory cytokines that are present in high levels in non-healing wounds and are thought to interfere with wound healing by destroying cytokines and other proteins essential to the wound healing process. Previous studies have demonstrated that the ratio of MMP-9 to TIMP-1 in wound fluids is inversely correlated with the healing of pressure wounds (Ladwig, G P, et al. Wound Rep Reg 2002, 10:26-37). Applicants have discovered that the physiologically relevant levels of TIMP-1 and TIMP-2 secreted by the cells of the invention, in particular AMP cells, and found in, for example, ACCS, block MMP activity and thus promote accelerated wound healing.

The compositions of the invention are applied in a therapeutically effective amount to accomplish accelerated wound healing, including increased wound strength and decreased wound failure. A "therapeutically effective amount" of a therapeutic agent within the meaning of the present invention will be determined by a patient's attending physician or veterinarian. Such amounts are readily ascertained by one of ordinary skill in the art and will enable accelerated wound healing when administered in accordance with the present invention. Factors which influence what a therapeutically effective amount will be include, the specific activity of the therapeutic agent being used, the wound type (mechanical or thermal, full or partial thickness, etc.), the size of the wound, the wound's depth (if full thickness), the absence or presence of infection, time elapsed since the injury's infliction, and the age, physical condition, existence of other disease states, and nutritional status of the patient. Additionally, other medication the patient may be receiving will effect the determination of the therapeutically effective amount of the therapeutic agent to administer.

In addition, compositions of the invention may play a role in more substantial wound healing, such as in the regeneration of limbs. US2003/0212024, which is incorporated by reference herein, sets forth methods of testing for such ability by measuring regeneration in the zebrafish, which is capable of complete regeneration following amputation of the distal fin. Following amputation, complete regeneration occurs in several steps, including formation of a wound epidermis, migration of fibroblasts and scleroblasts (or osteoblasts) toward the wound epidermis, formation of a blastema, and outgrowth of the blastema via cell division and differentiation of the proximal portion of the fin to form specific structures of the regenerated fin.

In a preferred embodiment of the present invention, ECS cells and conditioned media derived therefrom, including AMP cells and/or ACCS derived therefrom, and/or cell lysates thereof should be topically administered to the wound site to promote accelerated wound healing in the patient. This topical administration can be as a single dose or as repeated doses given at multiple designated intervals. It will readily be appreciated by those skilled in the art that the preferred dosage regimen will vary with the type and severity of the injury being treated.

Formulations suitable for topical administration in accordance with the present invention comprise therapeutically effective amounts of the therapeutic agent with one or more pharmaceutically acceptable carriers and/or adjuvants. ECS cells and conditioned media derived therefrom, including AMP cells and/or ACCS derived therefrom, and/or cell lysates thereof may be used in conjunction with a variety of materials routinely used in the treatment of wounds, such as collagen based creams, films, microcapsules, or powders; hyaluronic acid or other glycosaminoglycan-derived preparations; creams, foams, suture material; and wound dressings. Alternatively, the ECS cells and conditioned media derived therefrom, including AMP cells and/or ACCS derived therefrom, and/or cell lysates thereof can be incorporated into a pharmaceutically acceptable solution designed for topical administration.

Reconstructive and cosmetic surgery—The compositions and methods of the present invention are effective in accelerating healing following reconstructive and cosmetic surgery. It's estimated that more that one million reconstructive procedures are performed by surgeons every year. The goals of reconstructive surgery differ from those of cosmetic surgery. Reconstructive surgery is performed on abnormal structures of the body, caused by birth defects, developmental abnormalities, trauma or injury, infection, tumors, or disease. It is generally performed to improve function, but may also be done to approximate a normal appearance. Cosmetic surgery is performed to reshape normal structures of the body to improve the patient's appearance and self-esteem (i.e. rhinoplasty).

Reconstructive surgery is used to correct congenital deformities (i.e. birth defects such as birthmarks; cleft-lip and palate; syndactyly (webbed fingers); extra or absent fingers; and abnormal breast development) and deformities acquired as a result of accident, infection, disease, or in some cases, aging (i.e. burn wounds, lacerations, growths, and aging problems such as drooping eyelids which can impair vision). In each case, the reconstructive surgery requires not only repair of the surgical wounds, but often regeneration of tissue (i.e. bone or cartilage) and/or tissue growth to incorporate implant material, etc.

Keloid and/or Hypertrophic Scarring—The compositions and methods of the present invention are also effective in preventing or treating keloid and/or hypertrophic scars. Keloid and/or hypertrophic scars are abnormal scars that grow beyond the boundary of the original site of a skin injury. Although anyone can form a keloid and/or hypertrophic scar some ethnic groups are at more risk of developing them (i.e. keloid and/or hypertrophic scars are more common in pigmented ethnic groups rather than in Caucasians). It is not fully understood why or how keloid and/or hypertrophic scars occur. Skin trauma appears to be the most common factor although they can form even when there appears to be no apparent cause. Skin and/or muscle tension seem to contribute to keloid and/or hypertrophic scar formation and this is demonstrated by the most common sites of their formation (the upper arm and back). However other factors are involved. Infection at a wound site, repeated trauma to the same area or a foreign body in a wound can also be factors. There appears to be a genetic component to keloid and/or hypertrophic scarring and individuals whose family members form keloid and/or hypertrophic scars are at an increased risk of forming them themselves. Other theories for the causes of keloid and/or hypertrophic scarring include a deficiency or an excess in melanocyte hormone (MSH), decreased percentages of mature collagen and increased soluble collagen, or that very small blood vessels get blocked and the resulting lack of oxygen contribute to keloid and/or hypertrophic scar formation.

Current treatments for keloid and/or hypertrophic scars include surgical removal, non-surgical interventions and combination treatments. Surgical treatment of keloid and/or hypertrophic scars is the most effective and the least complex of the available forms of treatment, although the recurrence rate is high. Lasers have been tried as an alternative to traditional surgery but so far the outcomes are no better. Non surgical treatments for keloid and/or hypertrophic scars include interferon therapy and have been reported as effective in reducing keloid and/or hypertrophic scarring. However, such treatment has significant side effects (i.e. toxicity, flu-like symptoms, depression, nausea and vomiting). Prolonged compression of scar tissue can theoretically soften and break up keloid and/or hypertrophic scars, however the practicality of this option depends on the location of the keloid and/or hypertrophic scars. Other non-surgical interventions that are currently being tried with varying results include antihistamines, vitamins, nitrogen mustard, Verapamil, retinoic acids. Combined treatments for keloid and/or hypertrophic scarring include surgical removal of scar tissue in combination with a steroid injection. This type of treatment is variously reported as having between a 50% to 70% rate of recurrence. Another option combines surgery with external type radiotherapy. Radiation has the effect of interfering with skin growth (fibroblasts) and collagen production. Research varies on which type of combination therapy is the more effective.

Surgical adhesions. The compositions and methods of the present invention are also effective in preventing or treating surgical adhesions. Adhesions are internal scars made of strand like fibrous tissue that forms an abnormal bond between two parts of the body after trauma, injury, and/or surgery and in some cases may cause severe clinical consequences including severe pelvic pain, infertility and intestinal obstruction.

Any peritoneal injury can result in fibrous adhesion formation. For example, infection, endometriosis, chemotherapy, radiation and cancer may damage tissue and initiate adhesion formation. However, the most common cause of adhesion formation is surgery. Adhesions normally occur at the site of the surgical procedure and are a result of the body's normal healing process. Surgical procedures most commonly associated with adhesion formation are ovarian cystectomy, myomectomy, total abdominal hysterectomy, salpingostomy/fimbrioplasty, excision of endometriosis, excision of eptopic pregnancy, cesarean section, and adhesiolysis.

Following reproductive pelvic surgery performed by laparotomy, more than 50% of patients are shown to have adhesions at subsequent surgeries. The number of hospital readmissions for adhesion-related complications rivals the number of operations for heart bypass, hip replacements and appendectomies. It is not unusual for several organs to be adhered to each other causing traction (pulling) of nerves. Nerve endings may also become entrapped within a developing adhesion causing severe pain. Intestinal obstruction is one of the most severe consequences of adhesions. Adhesions can form elsewhere such as around the heart, spine and in the hand where they may lead to other problems.

Dental applications. The compositions and methods of the present invention are also effective in the treatment of many dental diseases and disorders including, for example, periodontal disease and healing following tooth extraction. Periodontal disease is common in the United States and throughout the world, and is a significant public health issue in many areas. Damage that occurs early in the course of disease, such as that caused by gingivitis or moderate periodontitis, can often be reversed or at least its progression stopped by aggressive treatment, including root scraping, surgery and antibiotic treatments. However, with more advanced periodontal disease it is usually impossible to effectively treat and, therefore, requires the rebuilding of portions of the tooth and root system and the upper and lower jaw bones with synthetic materials, or by bone or skin grafts. While these treatments have improved significantly, but they do not bring teeth, bone and gums back to normal. As a consequence, patients continue to have difficulties eating, may have distorted jaws. It is also possible the dental disease can lead to other medical problems, including infections and heart problems.

Peptic Ulcer Disease (PUD)—The compositions and methods of the present invention are also effective in the treatment of peptic ulcer disease. A peptic ulcer is an ulcer of one of those areas of the gastrointestinal tract that are usually acidic. Most peptic ulcers arise in the duodenum rather than in the stomach. Furthermore, most peptic ulcers are associated with *Helicobacter pylori*, a spiral-shaped bacterium that lives in the acidic environment of the stomach. Ulcers can also be caused or worsened by drugs such as Aspirin and other non-steroidal anti-inflammatory drugs.

Dermatological Applications and Cosmeceuticals. The same properties that make ECS cells and conditioned media derived therefrom, including AMP cells and/or ACCS derived therefrom, and/or cell lysates thereof, alone or in combination, as well as compositions of ECS cells as defined herein useful for wound healing make them similarly well-suited for the treatment of cosmetic and/or dermatological conditions, including aging skin. The dermal layer of skin, important in maintaining the elasticity and appearance of the skin, thins with age, leading to sagging and wrinkles.

As described above, fetal skin has much more effective repair mechanisms than adult skin, and, once wounded, in the first two trimesters of pregnancy, it is able to heal without the formation of scars. This capability does appear to require the fetal immune system, fetal serum, or amniotic fluid (Bleacher J C, et al., J Pediatr Surg 28: 1312-4, 1993); Ihara S, Motobayashi Y., Development 114: 573-82. 1992). Such abilities of fetal tissue have led to the suggested use of compounds produced by fetal tissue for regenerating and/or improving the appearance of skin (see, for example, US 2004/0170615, which is incorporated by reference in its entirety herein).

The present invention contemplates the use of the ECS cells and conditioned media derived therefrom, including AMP cells and/or ACCS derived therefrom, and/or cell lysates thereof, in the use of novel cosmetic skin care compositions. Such compounds may be delivered to skin by way of, but not limited to, a solution, a lotion, an ointment, a cream, a gel, or a skin peelable strip.

The methods generally include the step of topically applying a safe and effective amount of the composition to the skin of a mammal in need thereof. Additional skin care components, as well as cosmetically acceptable, dermatologically acceptable or pharmaceutically acceptable carriers may be included in such compositions.

Cosmetic compositions usually comprise an aqueous phase that is gelled, i.e. thickened, using one or more thickener(s) or gelling agent(s). These may be, for example, lotions which are aqueous solutions not containing an oily phase, or emulsions which may be direct oil-in-water emulsions including a fatty phase or oily phase dispersed in an aqueous continuous phase, or water-in-oil reverse emulsions including an aqueous phase dispersed in an oily continuous phase. The term "emulsions" means herein both the dispersions obtained in the absence of emulsifying surfactants and the emulsions obtained in the presence of emulsifying surfactants.

Oil-in-water emulsions are the emulsions most frequently sought in cosmetics due to the fact that, when applied to the skin, they give a softer, less greasy, fresher and lighter feel than water-in-oil emulsion systems, by virtue of the presence of water in the continuous outer phase.

The nature of the compounds used for gelling the aqueous phase and their content in the composition are chosen as a function of the desired type of texture, which may range from fluid lotions to more or less thick emulsions that may constitute milks or creams. The main thickeners or gelling agents used in cosmetics are chosen from the following compounds natural polymers such as xanthan gum and guar gum or cellulose derivatives, starches and alginates and crosslinked polymeric gelling agents such as the Carbopols or crosslinked and at least partially neutralized 2-acrylamido-2-methylpropanesulfonic acid polymers.

Differentiation of ECS Cells, Including AMP Cells, and Differentiated Cell Types The ECS cells, including AMP cells, may be contacted with various growth factors (termed differentiation factors) that influence differentiation of such stem cells into particular cell types such as skin cells, muscle cells, bone cells and nerve cells.

The literature is replete with differentiation protocols for embryonic as well as non-embryonic stem or other multipotent cells, including stem cells (see for example osteogenic differentiation (Shi, Y. Y., et al., (2005) Plast Reconstr Surg 116, 1686-96.); adipogenic differentiation (Shi, Y. Y., et al., (2005) Plast Reconstr Surg 116, 1686-96.); chondrogenic differentiation (Malladi, P., et al., (2006) Am J Physiol Cell Physiol 290, C1139-46.). One skilled in the art will recognize that any of these protocols may be applied to the ECS cell compositions, including the AMP cell compositions described herein to produce partially or fully differentiated cells for such uses.

Differentiated cells derived from ECS cells including AMP cells may be detected and/or enriched by the detection of tissue-specific markers by immunological techniques, such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods.

Alternatively, differentiated cells may be detected using selection markers. For example, AMP cells can be stably transfected with a marker that is under the control of a tissue-specific regulatory region as an example, such that during differentiation, the marker is selectively expressed in the specific cells, thereby allowing selection of the specific cells relative to the cells that do not express the marker. The marker can be, e.g., a cell surface protein or other detectable marker, or a marker that can make cells resistant to conditions in which they die in the absence of the marker, such as an antibiotic resistance gene (see e.g., in U.S. Pat. No. 6,015,671).

Isolation, Identification and Characterization of ECS Cells Including AMP Cells

Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666,949, 60/699,257, 60/742,067, 60/813,759, U.S. application Ser. Nos. 11/333,849, 11/392,892, PCTUS06/011392, US2006/0078993, PCT/US00/40052, U.S. Pat. No. 7,045,148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete a unique combination of cytokines into the extracellular space or into surrounding culture media. Suitable cells are those in which the cytokine or cytokines occurs in the physiological range of ~5.0-16 ng/ml for VEGF, ~3.5-4.5 ng/ml for Angiogenin, ~100-165 pg/ml for PDGF, ~2.5-2.7 ng/ml for TGFβ2, ~0.68 μg ml for TIMP-1 and ~1.04 μg/ml for TIMP-2.

In a particular embodiment, AMP cell compositions are prepared using the steps of a) recovery of the amnion from the placenta, b) dissociation of the cells from the amniotic membrane, c) culturing of the cells in a basal medium with the addition of a naturally derived or recombinantly produced human protein; and optionally d) further proliferation of the cells using additional additives and/or growth factors. Details are contained in US Publication No. 2006-0222634-A1, which is incorporated herein by reference.

In a preferred embodiment, the following method is used to obtain selected AMP cells. The cells are plated into plastic tissue culture vessels (i.e. T75 flasks) immediately upon isolation from the amnion. After ~1-5 days, preferably ~1-3 days, and most preferably ~2 days in culture, non-adherent cells are removed from the plastic tissue culture vessel and discarded and the adherent cells are kept. This attachment of cells to a plastic tissue culture vessel is the selection method used to obtain the desired population of AMP cells. Adherent and non-adherent AMP cells appear to have similar cell surface marker expression profiles but the adherent cells have the advantage of possessing greater viability than the non-adherent population of cells and are thus the desired population of AMP cells. Adherent AMP cells are cultured until they reach ~13,000-700,000 cells/cm$^2$, preferably ~53,000-500,000 cells/cm$^2$ and most preferably ~120,000-300,000 cells/cm$^2$. At this point, the cultures are confluent or close to confluent. Suitable cells cultures will reach this number of cells between ~5-14 days, preferably between 5-9 days. Attaining this criterion is an indicator of the proliferative potential of the AMP cells and cells that do not achieve this criterion are not selected for further analysis and use. Once the AMP cells reach ~13,000-700,000 cells/cm$^2$, preferably ~53,000-500,000 cells/cm$^2$ and most preferably ~120,000-300,000 cells/cm$^2$, they are removed from the plastic tissue culture vessel and cryopreserved. This collection time point is called p0 and all subsequent analyses are done with thawed p0 AMP cells.

The AMP cells of the invention are characterized by assaying for physiologically relevant cytokines. Suitable cells are those in which each cytokine occurs in the physiological range of ~5.0-16 ng/ml for VEGF, ~3.5-4.5 ng/ml for Angiogenin, ~100-165 pg/ml for PDGF, ~2.5-2.7 ng/ml for TGFβ2, ~0.68 μg/ml for TIMP-1 and ~1.04 μg/ml for TIMP-2.

In addition, the AMP cells of the invention are further characterized as follows: Using commercially available antibodies to known stem cell markers, freshly isolated AMP cells have been extensively characterized. Briefly, freshly isolated AMP cells are substantially negative with respect to CD90 and CD117. In addition, such cell populations are essentially negative for protein expression of CD34, CD44, CD45, CD140b, CD105; essentially positive for protein expression of CD9 and CD29; between about 70-95% positive for protein expression of SSEA4, CD10, CD166 and CD227; between about 60-95% positive for protein expression of HLA-G, EGFR and CD26; and between about 10-50% positive for protein expression of CD71. Details on this procedure are contained in US Publication No. 2006-0222634-A1, which is incorporated herein by reference.

In alternative embodiments substantially purified AMP cell populations can be created using antibodies against protein markers expressed (positive selection) or not expressed (negative selection) on the cell surface of the AMP cells. These antibodies may be used to identify, characterize, isolate or create such substantially purified populations of AMP cells expressing those protein markers using a variety of methods. Details on this procedure are contained in US Publication No. 2006-0222634-A1, which is incorporated herein by reference.

In addition, protein markers that are not expressed on the surface of AMP cells may also be used to identify, isolate or create populations of AMP cells not expressing those markers. Such procedures may involve a negative selection method, such as passage of sample cells over a column containing anti-protein marker antibodies or by binding of cells to magnetic bead-conjugated antibodies to the protein markers or by panning on plates coated with protein marker antibodies and collecting the unbound cells. Alternatively, a single-cell suspension may be exposed to one or more fluorescent-labeled antibodies that immuno-specifically bind to the protein markers. Details on this procedure are contained in US Publication No. 2006-0222634-A1, which is incorporated herein by reference.

Expanded Populations of ECS Cells, Including AMP Cells. One of skill in the art will recognize that any of the ECS cells of the instant invention may be expanded using the methods described below.

As described herein and in US Publication No. 2006-0222634-A1, which is incorporated herein by reference, Applicants have discovered a novel method for isolation and propagation of multipotent, AMP cells. Such methods result in AMP cell compositions which are expanded for multipotent cells, thereby providing, for the first time, sufficient quantities of cells to enable therapeutic cell transplantation. Expanded AMP cell compositions, which are made in accordance with the subject invention, are compositions in which the level of cells per gram of amniotic tissue is at least 50 fold and up to 150 fold higher after 5 passages, as compared to about 20 fold using previous methods. Alternatively, expanded AMP cell compositions, which are made in accordance with the subject invention, are compositions in which the level of cells per gram of amniotic tissue is at least 30 fold and up to 100 fold higher after 3 passages.

Additionally, the methods used for cell culture and proliferation provide a means to culture the cells, as well as other cells including but not limited to multipotent, pluripotent cells or totipotent cells, including, but not limited to, embryonic stem cells, in an animal-free system. Furthermore, the culture conditions described provide a cell that is less dependent on attachment to a culture surface for viability, thus allowing for propagation of the cells using suspension culture for efficient scale-up. Details on this procedure are contained in US Publication No. 2006-0222634-A1, which is incorporated herein by reference.

The expanded AMP cell compositions described herein demonstrate extensive proliferative potential, express certain genes known to be expressed only in undifferentiated cells (i.e. Nanog and Oct-4) and can differentiate into cell types that normally arise from all three embryonic germ layers (endoderm, ectoderm and mesoderm). This differentiation potential suggests that these expanded AMP cells may be able to contribute to a variety of cell types. The AMP cell compositions described herein are also useful as feeder layers for the growth of a variety of cell types, including but not limited to embryonic stem cells (ES cells). AMP cells, including those described herein, also produce a wide variety of cytokines and growth factors, thereby making both the cell compositions, conditioned media derived from the cells (ACCS), cell lysates therefrom, extracellular matrices produced by the cells, and combinations thereof useful for a variety of therapeutic applications, in particular cell-based therapeutic applications such as transplantation therapies.

Culturing of the AMP cells—The cells are cultured in a basal medium. Such medium includes, but is not limited to, Epilife (Cascade Biologicals), Opti-pro, VP-SFM, IMDM, Advanced DMEM, K/O DMEM, 293 SFM II (all made by Gibco; Invitrogen), HPGM, Pro 293S-CDM, Pro 293A-CDM, UltraMDCK, UltraCulture (all made by Cambrex), Stemline I and Stemline II (both made by Sigma-Aldrich), DMEM, DMEM/F-12, Ham's F12, M199, and other comparable basal media. Such media should either contain human protein or be supplemented with human protein. As used herein a "human protein" is one that is produced naturally or one that is produced using recombinant technology. "Human protein" also is meant to include a human fluid or derivative or preparation thereof, such as human serum or amniotic fluid, which contains human protein. Details on this procedure are contained in US Publication No. 2006-0222634-A1, which is incorporated herein by reference.

In a most preferred embodiment, the cells are cultured using a system that is free of animal products to avoid xeno-contamination. In this embodiment, the culture medium is Stemline I or II, Opti-pro, or DMEM, with human albumin added up to concentrations of 10%. Alternatively, UltraCulture may be used, with substitution of transferrin with human recombinant transferrin, and replacement of the bovine albumin (BSA) with human albumin at concentrations of up to 10%. The invention further contemplates the use of any of the above basal media wherein animal-derived proteins are replaced with recombinant human proteins and animal-derived serum, such as BSA, is replaced with human albumin. In preferred embodiments, the media is serum-free in addition to being animal-free. Details on this procedure are contained in US Publication No. 2006-0222634-A1, which is incorporated herein by reference.

In alternative embodiments, where the use of non-human serum is not precluded, such as for in vitro uses, the culture medium may be supplemented with serum derived from mammals other than humans, in ranges of up to 40%.

Additional proliferation—Optionally, other proliferation factors are used. In one embodiment, epidermal growth factor (EGF), at a concentration of between 0-1 μg/ml is used. In a preferred embodiment, the EGF concentration is around 10 ng/ml. Alternative growth factors which may be used include, but are not limited to, TGFα or TGFβ (5 ng/ml; range 0.1-100 ng/ml), activin A, cholera toxin (preferably at a level of about 0.1 μg/ml; range 0-10 μg/ml), transferrin (5 μg/ml; range 0.1-100 μg/ml), fibroblast growth factors (bFGF 40 ng/ml (range 0-200 ng/ml), aFGF, FGF-4, FGF-8; (all in range 0-200 ng/ml), bone morphogenic proteins (i.e. BMP-4) or other growth factors known to enhance cell proliferation.

Generation of ACCS—The AMP cells of the invention can be used to generate ACCS. In one embodiment, the AMP cells are isolated as described herein and $10 \times 10^6$ cells are seeded into T75 flasks containing between 5-30 ml culture medium, preferably between 10-25 ml culture medium, and most preferably about 10 ml culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, are also contemplated by the methods of the invention. It is also contemplated by the instant invention that the ACCS be cryopreserved following collection.

Compositions—The compositions of the invention include substantially purified populations of ECS cells, conditioned media derived therefrom, cell lysates derived therefrom and cell products derived therefrom, and pharmaceutical compositions of such. In preferred embodiments, the substantially purified populations of ECS cells are AMP cells, ACCS, cell lysates derived therefrom, cell products derived therefrom, and pharmaceutical compositions of such. The compositions of the invention can be prepared in a variety of ways depending on the intended use of the compositions. For example, a composition useful in practicing the invention may be a liquid comprising an agent of the invention, i.e. a substantially purified population of AMP cells, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like. In a particularly preferred embodiment, the liquid composition may contain ACCS.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions—The present invention provides pharmaceutical compositions of substantially purified populations of ECS cells, conditioned media derived therefrom, cell lysates derived therefrom and cell products derived therefrom, and a pharmaceutically acceptable carrier. The present invention also provides pharmaceutical compositions of substantially purified populations of AMP cells, ACCS, cell lysates derived therefrom, cell products derived therefrom, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture comprising packaging material and a pharmaceutical composition of the invention contained within the packaging material, wherein the pharmaceutical composition comprises a substantially purified population of ECS cells, conditioned media derived therefrom, cell lysates derived therefrom and cell products derived therefrom. In preferred embodiments, the substantially purified populations of cells are AMP cells, ACCS, cell lysates derived therefrom, cell products derived therefrom. In a particularly preferred embodiment, the composition is ACCS. The packaging material comprises a label or package insert which indicates that the substantially purified population of ECS cells, conditioned media derived therefrom, cell lysates derived therefrom and cell products derived therefrom, or AMP cells, ACCS derived therefrom, cell lysates derived therefrom and cell products derived therefrom can be used for treating a variety of disorders including but not limited to accelerating wound healing, preventing or reducing wound healing failure, scarring, etc.

Formulation, Dosage and Administration

Compositions comprising ECS cells, conditioned media derived therefrom, cell lysates derived therefrom and cell products derived therefrom, and in preferred embodiments substantially purified populations of cells are AMP cells, ACCS, cell lysates derived therefrom, cell products derived therefrom, may be administered to a subject to provide various cellular or tissue functions, for example, to accelerate wound healing. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in wound healing, tissue regeneration, or restoring a therapeutically important metabolic function. The compositions may also be administered to the recipient in one or more physiologically acceptable carriers. Carriers for the cells may include but are not limited to solutions of phosphate buffered saline (PBS) or lactated Ringer's solution containing a mixture of salts in physiologic concentrations.

One of skill in the art may readily determine the appropriate concentration, or dose, of ECS cells, including AMP cells and/or ACCS and/or lysates and/or cell products derived therefrom, for a particular purpose. The skilled artisan will recognize that a preferred dose is one which produces a therapeutic effect, such as accelerating wound healing, in a patient in need thereof. Determination of a preferred dose is based on the specific activity of the ECS cells, including AMP cells, and ACCS. Specific activity can be readily determined by assaying the potential of AMP cells and/or ACCS to stimulate cell proliferation in standard proliferation assays which are well known to skilled artisans (see, for example, Nissen, N. N., et al., J Trauma 2003; 54:1205-1211, incorporated herein in its entirety). Further, proper doses of ECS cells, including AMP cells and/or ACCS and/or lysates and/or cell products derived therefrom will require empirical determination at time of use based on several variables including but not limited to the severity and type of wound being treated; patient age, weight, sex, health; other medications and treatments being administered to the patient; and the like. For AMP cells a preferred dose is in the range of about 10-300,000 cells/µl vehicle. Another preferred dose is in the range of about 100-30,000 cells/µl vehicle. Another preferred dose is in the range of about 1000-3000 cells/µl vehicle. In a particular preferred embodiment, it has been found that relatively small amounts of AMP cells can accelerate wound healing, etc. One of skill in the art will also recognize that number of doses (dosing regimen) to be administered needs also to be empirically determined based on, for example, severity and type of wound being treated. In a preferred embodiment, one dose is sufficient to accelerated wound healing. Other preferred embodiments contemplate, 2, 3, 4, or more doses to accelerate wound healing, etc.

In addition, one of skill in the art may readily determine the appropriate concentration, or dose, of conditioned media, including, for example, ACCS, for a particular purpose. A preferred dose is in the range of about 0.5-2000 µl/cm$^2$. Another preferred dose is in the range of about 5-1000 µl/cm$^2$. Another preferred dose is in the range of about 50-100 µl/cm$^2$. In a particularly preferred embodiment, it has been found that relatively small amounts of ACCS can accelerate wound healing, etc. One of skill in the art will also recognize that number of doses (dosing regimen) to be administered needs also to be empirically determined based on, for example, severity and type of wound being treated. In a preferred embodiment, one dose is sufficient to accelerated wound healing. Other preferred embodiments contemplate, 2, 3, 4, or more doses to accelerate wound healing, etc.

Skilled artisans will recognize that any and all of the standard methods and modalities for wound healing currently in clinical practice and clinical development are suitable for practicing the methods of the invention. Routes of administration, formulation, co-administration with other agents (if appropriate) and the like are discussed in detail elsewhere herein.

Timing of treatment and administration of the compositions of the invention is also dependent upon the severity and type of wound being treated. For example, for surgical wounds it may be advantageous to treat, or prime, the surgical site prior to incisional injury. It may also be advantageous to treat the surgical site post-surgery. It may also be advantageous to treat the surgical site during surgery. Other embodiments contemplate different dosing intervals (i.e. prior to surgery and/or during surgery and/or after surgery). In the case of traumatic wounds, when treatment is only possible after the injury has occurred, it may be advantageous to treat the wound immediately upon presentation and again following medical and/or surgical intervention. Attending physicians will determine the exact treatment regimen based on the severity of the wound being treated, etc.

It may be desirable to administer ECS cells and/or conditioned media derived therefrom and/or cell lysates derived therefrom and/or cell products derived therefrom, including AMP cells, and/or ACCS and/or cell lysates derived therefrom and/or cell products derived therefrom in combination with other agents, including active agents and/or inactive agents. Active agents include but are not limited to growth factors, cytokines, chemokines, antibodies, antibiotics, anti-fungals, anti-virals, other cell types, and the like. Inactive agents include carriers, diluents, stabilizers, gelling agents, delivery vehicles, ECMs (natural and synthetic), scaffolds, and the like.

ECS cells and/or conditioned media derived therefrom and/or cell lysates derived therefrom and/or cell products derived therefrom, including AMP cells, and/or ACCS and/or cell lysates derived therefrom and/or cell products derived therefrom can be administered by injection into a target site of a subject, preferably via a delivery device, such as a tube, e.g., catheter. In a preferred embodiment, the tube additionally contains a needle, e.g., a syringe, through which the cells can be introduced into the subject at a desired location. Specific, non-limiting examples of administering cells to subjects may also include administration by subcutaneous injection, intramuscular injection, or intravenous injection. For example, if administration is intravenous, an injectable liquid suspension of AMP cells and/or ACCS and/or lysates and/or cell products derived therefrom can be prepared and administered by a continuous drip or as a bolus.

ECS cells and/or conditioned media derived therefrom and/or cell lysates derived therefrom and/or cell products derived therefrom, including AMP cells, and/or ACCS and/or cell lysates derived therefrom and/or cell products derived therefrom may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating compositions as described herein, in a pharmaceutically acceptable carrier or diluent and, as required, other ingredients enumerated above, followed by filter sterilization.

Alternatively, ECS cells including AMP cells may be transplanted into the recipient where the cells will proliferate and differentiate to form new cells and tissues thereby providing the physiological processes normally provided by that tissue, or may produce factors that cause the migration and/or differentiation of cells in the area of the transplant. Tissues are an aggregation of similarly specialized cells united in the performance of a particular function. Tissue is intended to encompass all types of biological tissue including both hard and soft tissue. Soft tissue refers to tissues that connect, support, or surround other structures and organs of the body. Soft tissue includes muscles, tendons (bands of fiber that connect muscles to bones), fibrous tissues, fat, blood vessels, nerves, and synovial tissues (tissues around joints). Hard tissue includes connective tissue (e.g., hard forms such as osseous tissue or bone) as well as other muscular or skeletal tissue.

Support matrices into which the ECS cells and/or conditioned media derived therefrom and/or cell lysates derived therefrom and/or cell products derived therefrom, including AMP cells, and/or ACCS and/or cell lysates derived therefrom and/or cell products derived therefrom can be incorporated or embedded include matrices which are recipient-compatible and which degrade into products which are not harmful to the recipient. These matrices provide support and protection for ECS cells including AMP cells in vivo and are, therefore, the preferred form in which such cells are transplanted into the recipient subjects.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications, and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,701.

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that bioactive compounds can be incorporated directly into the support matrix so that they are slowly released as the support matrix degrades in vivo. As the cell-polymer structure is vascularized and the structure degrades, AMP cells may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immuno-modulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792, 525, 5,965,997, 4,879,237 and 4,789,734).

In another example, the undifferentiated, partially differentiated or fully differentiated ECS cells including AMP cells, may be transplanted in a gel matrix (such as Gelfoam from Upjohn Company) which polymerizes to form a substrate in which the cells can grow. A variety of encapsulation technologies have been developed (e.g. Lacy et al., Science 254:1782-84 (1991); Sullivan et al., Science 252:718-712 (1991); WO 91/10470; WO 91/10425; U.S. Pat. Nos. 5,837, 234; 5,011,472; 4,892,538). During open surgical procedures, involving direct physical access to the damaged tissue and/or organ, all of the described forms of undifferentiated, partially differentiated or fully differentiated ECS cell including AMP cell delivery preparations are available options. These cells can be repeatedly transplanted at intervals until a desired therapeutic effect is achieved.

The present invention also relates to the use of ECS cells including AMP cells in three dimensional cell and tissue culture systems to form structures analogous to tissue counterparts in vivo. The resulting tissue will survive for prolonged periods of time, and perform tissue-specific functions following transplantation into the recipient host. Methods for producing such structures are described in U.S. Pat. Nos. 5,624,840 and 6,428,802, which are incorporated herein in their entireties.

The three-dimensional matrices to be used are structural matrices that provide a scaffold for the cells, to guide the process of tissue formation. Scaffolds can take forms ranging from fibers, gels, fabrics, sponge-like sheets, and complex 3-D structures with pores and channels fabricated using complex Solid Free Form Fabrication (SFFF) approaches. Cells cultured on a three-dimensional matrix will grow in multiple layers to develop organotypic structures occurring in three dimensions such as ducts, plates, and spaces between plates that resemble sinusoidal areas, thereby forming new tissue. Thus, in preferred aspects, the present invention provides a scaffold, multi-layer cell and tissue culture system. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

Examples of such scaffolds include a three-dimensional stromal tissue or living stromal matrix which has been inoculated with stromal cells that are grown on a three dimensional support. The extracellular matrix proteins elaborated by the stromal cells are deposited onto the scaffold, thus forming a living stromal tissue. The living stromal tissue can support the growth of ECS cells including AMP cells or differentiated cells later inoculated to form the three-dimensional cell culture. Examples of other three dimensional scaffolds are described in U.S. Pat. No. 6,372,494.

The design and construction of the scaffolding to form a three-dimensional matrix is of primary importance. The matrix should be a pliable, non-toxic, injectable porous template for vascular ingrowth. The pores should allow vascular ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors to the cells on the interior of the matrix and to allow the ingrowth of new blood vessels and connective tissue. At the present time, a porous structure that is relatively resistant to compression is preferred, although it has been demonstrated that even if one or two of the typically six sides of the matrix are compressed, that the matrix is still effective to yield tissue growth.

The polymeric matrix may be made flexible or rigid, depending on the desired final form, structure and function. For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

A sponge-like structure can also be used to create a three-dimensional framework. The structure should be an open cell sponge, one containing voids interconnected with the surface of the structure, to allow adequate surfaces of attachment for sufficient ECS cells including AMP cells or differentiated cells to form a viable, functional implant.

The invention also provides for the delivery of ECS cells including AMP cells, including AMP cell compositions described herein, in conjunction with any of the above support matrices as well as amnion-derived membranes. Such membranes may be obtained as a by-product of the process described herein for the recovery of AMP cells, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, ECS cells including AMP cells may be grown on such membranes, added to the membrane in either an undifferentiated, partially differentiated or fully differentiated form, or ACCS or cell lysates may be added to such membranes. Alternatively, amniotic tissue in which AMP cells have not been stripped away may be used to deliver ECS cells including AMP cells to a particular site. In all cases, ECS cells including AMP cells used in conjunction with amniotic tissue or other matrices can be used in combination with other therapeutically useful cells and/or cells expressing biologically active therapeutics such as those described in below.

In another embodiment, the ECS cells, including AMP cells, can be used in combination with commercially available extracellular matrix products such as Oasis®, Dermagraft®, DressSkin®, Alloderm®, Promogran®, etc. For example, the ECS cells, including AMP cells, can be placed on top of these products and then applied to the wound to accelerate wound healing. Such application may occur immediately upon combining the products or after incubation for a period of time.

ECS cells, including AMP cells, may be genetically engineered to produce a particular therapeutic protein. Therapeutic protein includes a wide range of biologically active proteins including, but not limited to, growth factors, enzymes, hormones, cytokines, inhibitors of cytokines, blood clotting factors, peptide growth and differentiation factors. Particular differentiated cells may be engineered with a protein that is normally expressed by the particular cell type. For example, dermal cells can be engineered to produce collagen fibers and epidermal cells can be engineered to produce melanin.

Methods which are well known to those skilled in the art can be used to construct expression vectors containing a nucleic acid encoding the protein of interest linked to appropriate transcriptional/translational control signals. See, for example, the techniques described in Sambrook et al, 2001, "Molecular Cloning: A Laboratory Manual"; Ausubel, ed., 1994, "Current Protocols in Molecular Biology" Volumes I-III; Celis, ed., 1994. Details on this procedure are contained in US Publication No. 2006-0222634-A1, which is incorporated herein by reference.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Recovery of AMP cells—AMP cells were dissociated from starting amniotic membrane using the dissociation agents PXXIII, and trypsin. The average weight range of an amnion was 18-27 g. The number of cells recovered per g of amnion was about $10\text{-}15 \times 10^6$ for dissociation with PXXIII and $5\text{-}8 \times 10^6$ for dissociation with trypsin.

Culture conditions—The primary AMP cells were cultured for 5 passages in the following media: Stemline II+10% FBS, Stemline II+10% plasbumin (pb), Ultraculture+10% plasbumin (pb), and DMEM+10% FBS. Each culture condition was tested using 15 million cells/g amnion, 10 million cells/g amnion, and 5 million cells/g amnion, depending on the enzyme used for recovery of the primary cells. For instance, using PXXIII, 15 million cells/g amnion were obtained, while using trypsin, 10 million cells/g amnion were obtained, while other enzymes resulted in even lesser recovery (5 million cells/g amnion).

Passaging—Cells were passaged 5 times as follows: The cells were grown attached to a culture flask (on tissue culture treated plastic). The cells were left to divide and grow. The cells were removed from the plastic using Tryple™ (Invitrogen), a trypsin-like product that is animal-free GMP grade. Once unattached, the cells were centrifuged, and the cell pellet removed and resuspended in the culture medium with protein and additives (10 ng/ml EGF) and replated back onto fresh flasks. Cells were grown in a humidified atmosphere at 37° C. and 5% $CO_2$.

The results indicate that the use of either Stemline or Ultraculture with added plasbumin (pb) or albumin, the primary cultures are expanded to a level that is at least 4 fold and as much as 10 fold higher than is obtained using previous methodology (DMEM with fetal bovine serum). Even the use of plasbumin (pb) in the basal media DMEM resulted in an expanded AMP cell composition, having a 3-fold increase in multipotent cells as compared to the previous method of using DMEM with fetal bovine serum. Details on these results are contained in US Publication No. 2006-0222634-A1, which is incorporated herein by reference.

Another significant result observed was that cells grown in medium containing plasbumin displayed a spheroidal phenotype after passaging. When the AMP cells were removed from the tissue culture surface with the digestive enzyme and replated, AMP cells formed small clusters of cells that were not firmly adhered to the culture surface. Some of the clusters of cells were completely in suspension. These AMP cell clusters proliferated until up to 200 cells were present in the clusters. After a period of 1-5 days, the clusters of cells reattached and flattened out to form an adherent monolayer. This clustering phenotype was observed at each passage. Further studies indicated that such clustering occurs in the following media containing either recombinant human albumin, plasbumin, or plasmanate: OptiPRO SFM, VP-SFM, Iscove's MDM, HPGM, UltraMDCK, Stemline II and Stemline I, DMEM, and DMEM:F12, but not in Advanced DMEM, Knockout DMEM, 293 SFM II, Pro 293S-CDM, Pro 293A-CDM or Ultraculture VP-SFM.

Example 2

Use of AMP Cell and ACCS Compositions in Wound Healing

Methods. The keratinocyte cell line isolated from epidermis (ATCC CRL-1555) was seeded onto 6-well plates at a density of $0.3 \times 10^6$ cells per well. Cells were left to grow to confluency then placed into serum-free conditions for 48 hours. In each well a scrape or wound of the confluent monolayer was made from the top to the bottom of the well using a 1 ml pipette tip. Images of the scrape were taken at 0, 24, 30 and 48 hours to determine cell migration or percent of wound closure in response to addition of ACCS to each well. Conditions tested were 0%, 50%, and 100% of the following: 1) No ACCS (control, 0%); 2) ACCS from AMP cells passaged normally at ratio of 1:3; 3) ACCS from AMP cells that were never passaged; 4) ACCS from AMP cells grown in the ATCC cells' media; and 5) Conditioned media from ATCC cells grown in their own media. Approximately 6 measurements were taken in microns of each scrape at each time point using phase microscopy and MetaMorph imaging software. The percent of healing was calculated by comparing the width of each wound at 24, 30, and 48 hours to the starting width of the wound at time zero.

Results. ACCS from AMP cells showed a significant increase in cell migration or healing of the scrape compared to control. CM from other cell types, however, did not show this increase. Cells that grew in ACCS from AMP cells were the only condition that showed complete closure of the scrape before 24 hours. ACCS from cells passaged at a ratio of 1:3 and at a concentration of 50% (ACCS/non-CM) produced the best results. These results suggest that components of ACCS from AMP cells have properties that increase cell migration or wound healing.

Example 3

AMP Cells, ACCS, and Cell Lysates Accelerate Re-Epithelialization, Collagen Synthesis, and Regain to Tissue Tensile Strength The following experiment was done in an art-accepted animal model to assess whether the application of AMP cells, ACCS or AMP cell lysates could: 1) accelerate the rate of re-epithelialization, 2) accelerate collagen synthesis and deposition in the wound bed and 3) speed up regain to tissue tensile strength and demonstrate that transplantation of stem cells may have the same properties. It was also done to assess whether transplanted AMP cells could incorporate into epidermal and dermal structures including follicles, glands and blood vessels.

Skin wounding: A pair of 6 mm diameter wounds was made on each side of the dorsal midline. These wounds were full-thickness through the epidermis and dermis. Wounds were treated with: nothing (control), vehicle (10 mm Gelfoam sponge saturated with non-conditioned media), ACCS (10 mm Gelfoam sponge saturated with ACCS), hyaluronic acid vehicle (0.1 ml of Hylan A gel, Genzyme Corporation), hyaluronic acid+fluorescently (CM-DiI dye, Molecular Probes, Eugene Oreg.) labeled AMP cells ($10^6$ cells/wound) or hyaluronic acid+AMP cell lysate (from $10^6$ cells/wound), immediately following injury. The entire dorsal skin was covered with a sterile dressing and secured with a biocompatible adhesive (Mastisol, Ferndale Laboratories Inc, Ferndale, Mich.). Wounds in the first three treatment groups were re-treated in an identical manner on days 2, 3, 4 and 5 post wounding. Following the 5th wound treatment, the wounds were left undisturbed until day 7, at which time the Gelfoam as well as the sterile dressing was removed and the wound allowed to heal exposed to the surrounding environment. Wounds in the last three treatment groups were left undisturbed until time of sacrifice.

Imaging and clinical assessment: Two blinded observers assessed the degree of wound healing for each of the 180 wound samples at the following days post injury: 1, 2, 3, 4, 5, 7, 14 and 21. The following parameters were ascertained: hemostasis, wound contraction, re-epithelialization and inflammation. Digital images were taken of representative wound samples for each treatment group and stored for later analysis.

Tissue analysis: Animals were euthanized and dorsal skin was removed using aseptic technique and each wound was individually dissected and divided. One half of each wound was used for tensile strength measurements, with the other embedded for frozen sectioning and image analysis.

Tensiometry: Wound samples from the day 7, 14 and 21 groups were analyzed by tensiometry. The results for individual specimens from one wound were combined to determine an average TS/wound (tensile strength per wound). This value was normalized for the TS/skin (tensile strength of uninjured skin from the opposite side); TS/wound divided by TS/skin=relative TS/wound. The relative TS/wound was tabulated for each group at each time point and the mean and standard deviations determined using Excel database software (Microsoft Office 2000).

Microscopic analysis: Tissue specimens were embedded in O.C.T. (Miles, Inc., Elkhart, Ind.) and cryostat-sectioned into approximately 10 μm thick sections, at −23° C. Thin sections, mounted on glass microscope slides, were stored in moisture-proof slide boxes at −70° C. Representative slides were processed for immunohistochemical characterization of the connective tissue components using standard techniques. Hematoxylin and eosin staining were used to ascertain the overall histological appearance of the injured mucosa. Collagen presence in the wound was assayed using Masson's trichrome stain. Picrosirius-polarization method was used to analyze collagen fiber organization. Grafting and survival of fluorescently labeled stem cells in the wound bed was semi-quantitatively analyzed by measuring the total amount of fluorescence present in the wound bed. Localization of cells was recorded and analyzed.

Effect on the rate of wound re-epithelialization and dermal collagen deposition and organization was determined. Each of these, as well as other components of the wound healing process, were analyzed using specific markers. Transplantation of live AMP cells into the dermal wound bed was expected to result in: 1) differentiation and engrafting of stem cells into various skin compartments and 2) continual regulated release of various stem cell factors.

Results—Treatment of wounds with ACCS showed an increase in contracted granulation formation by Day 5, and smaller wounds, greater contraction and healing by Day 14. In addition, the wounds exhibited faster re-epithelialization and angiogenesis as compared to controls. Synthesis and deposition of collagen and regain of tissue tensile strength were unaltered over the course of the experiment. Treatment of wounds with AMP cells showed re-epithelialization and angiogenesis at early time points, as well as evidence of collagen deposition and organization. Engrafted cells were not detected. No differences based on visual inspection in clinical observations (redness, swelling, size, etc.) were seen nor was regain of tissue tensile strength altered over the course of the experiment.

Example 4

Detection of Cytokines in ACCS and Unconditioned Media Samples

In addition to multipotency, AMP cells may play a significant role in the inflammatory response. In the early phases of wound healing, chemokines and cytokines regulate chemotaxis and activation of inflammatory cells. Growth factors play dominant roles in regulating cell proliferation, differentiation, and synthesis of extracellular matrix. Amnion epithelial cells have been shown to secrete many cytokines and growth factors. These factors include prostaglandin E, PDGF, TGF-α, EGF, IL-4, IL-8, TNF, interferons, activin A, noggin, b-FGF, angiogenic factors, and other neuroprotective factors (Koyano, S., et al., (2002) Dev Growth Differ 44, 103-12; Blumenstein, M., et al., (2000) Placenta 21, 210-7; Tahara, M., et al., (1995) J Clin Endocrinol Metab 80, 138-46; Paradowska, E., et al., (1997) Placenta 18, 441-6; Denison, F. C., et al., (1998) Hum Reprod 13, 3560-5; Keelan, J. A., (1998) Placenta 19, 429-34; Sun, K., et al., (2003) J Clin Endocrinol Metab 88, 5564-71; Uchida, S., et al., (2000) J Neurosci Res 62, 585-90).

Many of these cytokines are associated with wound healing and some have been credited with contributing to scarless healing in the fetus (Robson, M. C., et al., (2001) Curr Probl Surg 38, 72-140; Ferguson, M. W. et al., (2004). Philos Trans R Soc Lond B Biol Sci 359, 839-50).

To determine which of these cytokines may be secreted by the AMP cells of the present invention, ACCS was isolated from cell cultures that were seeded onto tissue culture treated flasks at a density of ~40,000 cells per cm$^2$. Cells were cultured in a proprietary serum-free medium supplemented with 10 ng/ml of EGF. Culture media was exchanged every 2 days during the growth period. After cells reached near confluency (~1-2 wk after isolation), fresh media was applied and ACCS was collected after three days and stored at −80° C. for subsequent analysis.

ACCS was analyzed for secreted protein content via antibody arrays for multiple protein detection (RayBiotech, Norcross, Ga. using RayBio® Human Cytokine Antibody Arrays V, VI, and VII). The samples that were analyzed were complete unconditioned media+plasbumin; complete unconditioned media+EGF (no plasbumin); ACCS from placenta 1+plasbumin; ACCS from placenta 1 (no plasbumin); and ACCS from placenta 2+plasbumin.

Results—The following wound healing relevant cytokines were detected in ACCS by immunoblot: Angiopoietin-2, Angiogenin, bFGF, EGF, FGF-7, FGF-4, IGF-1, IL-1 beta, IL-2, IL-4, IL-6, IL-8, IL-10, PDGF-AA, PDGF-AB, PDGF-BB, PDGF-Ra, PDGF-Rb. The following wound healing relevant cytokines were not detected in ACCS by immunoblot: TGFα, TGFβ1, TGFβ2, TGFβ3.

Example 5

Detection of Cytokines in Non-Pooled and Pooled ACCS Using ELISA

ELISAs were performed on non-pooled and pooled ACCS because it is a more sensitive assay and because the results are quantitative. ELISAs were performed on conditioned media (ACCS) derived from AMP cells obtained from 10 different placentas (non-pooled ACCS). In addition to assaying each ACCS sample individually, pooled ACCS samples were also tested to determine if variability of ELISA results between samples could be reduced. ACCS was obtained as follows: AMP cells were isolated from the amnion as described in Example 1 above, seeded at 10×10$^6$ cells/10 ml media/T75 tissue culture flask and cultured until confluent. Once confluent, the media was changed and ACCS was collected 3 days post-confluence. ACCS was centrifuged to remove any cellular debris, aliquoted, and stored at −80° C. Pool 1 was comprised of ACCS from placentas 1-5, Pool 2 was comprised of ACCS from placentas 6-10, and Pool 3 was comprised of ACCS from placentas 1-10.

Results: In the non-pooled ACCS samples, PDGF levels ranged from about 75-165 pg/ml whereas in Pool 1, 2 and 3 the levels ranged from about 110-170 pg/ml. In the non-pooled ACCS samples, Angiogenin levels ranged from about 3.5-4.5 ng/ml whereas in Pool 1, 2 and 3 the levels ranged from about 3.5-4.5 ng/ml. In the non-pooled ACCS samples, VEGF levels ranged from about 4-18 ng/ml whereas in Pool 1, 2 and 3 the levels ranged from about 6-16 ng/ml. VEGF was not detected in the less sensitive immunoblot assay described in Example 4 above. In the non-pooled ACCS samples, TGF-β2 levels ranged from about 1-4.5 ng/ml whereas in Pool 1, 2 and 3 the levels ranged from about 2.5-2.7 ng/ml. TGFβ2 was not detected in the less sensitive immunoblot assay described in Example 4 above. In the non-pooled ACCS samples, TIMP-1 was 0.68 µg/ml (as measured by a multiplex assay). In the non-pooled ACCS samples, TIMP-2 level was 1.05 µg/ml. Pooling of ACCS had the effect of reducing variability of secreted factor levels as compared to those measured in the non-pooled ACCS samples. This creates a more consistent product that contains physiological levels of cytokines and growth factors similar to those reported in the literature for acute wound healing. It also provides an efficient method of creating the more consistent product, thus reducing manufacturing costs.

Example 6

AMP Cell/Fibroblast Co-Cultures to Create Amnion-Derived Multicellular Dressings (AMDs)

Co-cultures—It has been reported in the literature that under certain conditions when ES cells are co-cultured with fibroblasts, the ES cells are induced to differentiate into keratinocyte-like cells. To determine what effect co-culture of AMP cells with fibroblasts would have on AMP cells, an experiment was done in which $3.3 \times 10^6$ AMP cells were co-cultured with $0.4 \times 10^6$ fibroblasts on a collagen IV-coated T25 flask for 3, 5, 10, 15, and 25 days.

Results: When treated with the trypsin-like enzyme Tryple (Invitrogen), both AMP cell cultures and fibroblast cell cultures alone release cells as a single cell suspension. However, when the AMP cell/fibroblast co-culture was treated with Tryple, the cells came off the treated culture surface as sheets rather than as a single cell suspension. Furthermore, the sheets were very stable and somewhat resistant to enzymatic and mechanical disruption.

It is theorized that these sheets may be suitable for use as wound dressings when it is desirable to have a dermal-type graft. With demonstrated recent success with mitral resuscitation, management of inhalation injuries, control of burn wound sepsis, and understanding of the hypermetabolic response, early excision and rapid closure of the burn wound with a serviceable integument becomes a therapeutic imperative. In small surface area burns, this can be accomplished by autogenous skin grafts. For large surface area burns, both partial and full-thickness, there is not yet a totally satisfactory solution. Cutaneous epithelial autografts can be grown from the patient's skin and massively expanded to cover the entire body. Unfortunately, the lack of dermis leads to prolonged fragility and significant scarring, therefore, many believe that a "dermis" is required along with an epithelium.

Recent products with a supposed dermal substitute or neo-dermis such as Integra, Alloderm, Transcyte, Apligraf, and Dermagraft have attempted solve the problem. However, all of these "skin" substitutes have the problem of being expensive and having lower resistance to infection than autografts. Without a satisfactory rapid reliable wound closure for burn injuries, the wound remains in the inflammatory phase of healing for a prolonged period of time resulting in excessive scarring.

Robson et. al., (Robson, M. C., and Krizek, T. J. (1973) Ann Surg 177, 144-9.) reported success in treatment of experimental and clinical burns (both partial and full thickness) using human amniotic membranes. It was thought that part of the effect seen from the treatment with amniotic membranes was due to a humoral substance or substances stimulating wound healing. These observations were prior to present knowledge of cytokines and growth factors. More recently, attempts have been made to use recombinant growth factors and growth hormones to affect more rapid healing of the burn wound. Amniotic membranes proved not to be practical because of the risk of virally transmitted diseases. However, the observations from those early experiments and coupled with new knowledge support the possibility that the multipotentiality of AMP cells and their now demonstrated and described herein protein secretory profile of cytokines and other humoral substances stimulatory for wound healing may be useful in providing rapid early closure for thermal injuries.

Co-culture of AMP cells/fibroblasts on ECM to create amnion-derived multicellular dressings (AMDs): AMP cells were collected at T0 and seeded onto coated T25's tissue culture flasks at a density of $3.3 \times 10^6$. AMP cells were allowed to attach and begin to proliferate (1-2 days). Human foreskin fibroblasts were seeded into the same flask at a density of $0.2 \times 10^6$ (this density may be varied). Co-cultures were supplemented every other day with Celprogen stem cell keratinocyte differentiation media (other suitable media include but are not limit to EpiLife and UltraCulture). Co-cultures can be maintained up to 30 days or more. Transformation into removable 'sheet' of cells usually occurs around day 14 and can be assessed by observing cell morphology. The 'sheet' of cells was removed by incubation in Tryple (Invitrogen). The 'sheet' of cells was then placed on Oasis, a commercially available ECM (other suitable ECMs include but are not limited to Alloderm and DressSkin), and allowed to grow in differentiation conditions until an AMD formed, then fixed, and sectioned. The AMD was then assayed by IHC for differentiation markers and HE for organization and morphology.

Results: The results of this experiment demonstrated that AMP cells grow and proliferate to form a stratified phenotype on Oasis and Alloderm as determined by HE.

The above experiment was also be done with AMP cells collected at the end of p0 after having been primed in differentiation conditions before seeding on Oasis. The results of this experiment demonstrated that the cells attached to the Oasis and exhibited a stratified phenotype.

Example 7

Effects of ACCS in an Animal Model of Acute Wound Healing

An art-accepted animal model of acute excisional granulating wound was used to evaluate the effect of ACCS on wound healing. Details are contained in US Publication No. 2006-0222634-A1, which is incorporated herein by reference. The animals were divided into the following groups: Group I—ACCS, non-infected; Group II—Unconditioned media; Group III—ACCS, infected; Group IV—Unconditioned media, infected.

Analog tracings were made every 72 hours onto acetate sheets of both open wound areas and of the advancing full-thickness skin edges of all wounds. To eliminate site-related variability in the wounds, only the three caudal wounds were measured for statistical purposes, since the most cephalad wound has been shown to demonstrate different healing characteristics. Wound area calculations were performed with the use of digital planimetry (Sigma Scan; Jandel Scientific, Corte Modera, Calif.). Weekly quantitative bacterial analyses were performed on a subset of wounds in each group and are expressed as CFUs/g of tissue.

After all four wounds of each animal were completely epithelialized as determined by visual inspection, the animals were euthanized and the entire dorsum of the rat including the panniculus carnosus was removed. A 1 cm wide skin strip perpendicular to each resultant scar, was harvested for breaking strength analysis. An Instron tensiometer (Model No. 4201; Instron Corp., Canton, Mass.) with a 5 kg tension load cell and cross head speed of 10 mm/min was used. Breaking strength is defined as the force required to rupture the scar and is reported in kilograms.

Results—The application of ACCS overcomes the inhibition of wound healing caused by bacteria and shifts the healing trajectory in contaminated wounds to that of near normal healing.

Example 8

Effects of ACCS in an Animal Model of Chronic Wound Healing

An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.).

Results: ACCS was effective in not allowing proliferation of tissue bacterial bioburden. ACCS allowed accelerated healing of the granulating wound significantly faster than the non-treated infected control groups.

Example 9

Characterization of AMP Cells at p0

Method of obtaining selected AMP cells: Cells were plated immediately upon isolation from the amnion. After ~2 days in culture non-adherent cells were removed and the adherent cells were kept. This attachment to plastic tissue culture vessel is the selection method used to obtain the desired population of cells. Adherent and non-adherent AMP cells appear to have a similar cell surface marker expression profile but the adherent cells have greater viability and are the desired population of cells. Adherent AMP cells were cultured until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reach ~120,000-150,000 cells/cm$^2$, they were collected and cryopreserved. This collection time point is called p0 and all subsequent analyses are done with thawed p0 AMP cells.

Analysis of thawed p0 AMP cells: The AMP cells were analyzed for the expression of several cell surface markers. Table 1 below shows the results of this cell surface maker analysis as well as the % positive of these same markers upon isolation of the cells from the amnion. As can be seen, with the exception of HLA-G (whose expression goes down) and CD90 (whose expression goes up), the other tested cell surface markers remain constant over time.

TABLE 1

| Cell Surface Marker | % positive at isolation | % positive at p0 |
|---|---|---|
| CD90 | >95 | >95 |
| CD29 | >95 | >95 |
| SSEA4 | 70–90 | 70–90 |
| CD10 | 70–90 | 70–90 |
| CD44 | <1 | <1 |
| CD45 | <1 | <1 |
| HLA-G (MEMG/9 ab) | >60 | 10–50 |
| CD90 | <1 | 10–50 |

Example 10

Generation of ACCS

The AMP cells of the invention can be used to generate ACCS. The AMP cells were isolated as described herein and 10×10$^6$ cells were seeded into T75 flasks containing 10 ml culture medium. The cells are cultured until confluent, the medium is changed and ACCS was collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, are also contemplated by the methods of the invention. It is also contemplated by the instant invention that the ACCS be cryopreserved following collection.

Example 11

Effects of AMP Cells and ACCS in Two Animal Models of Wound Healing

The two art-accepted animal models of granulating wounds described above were used to evaluate the effect of AMP cells and ACCS on wound healing. The experimental groups for these experiments are Group I—Non-contaminated control (UCM only); Group II—Contaminated, ACCS; Group III Contaminated, AMP cells; Group IV—Contaminated AMP cells+ACCS; and Group V—Contaminated control.

Results: Neither ACCS, AMP cells, or AMPs cells+ACCS had any effect on bacterial load in the acute contaminated wound model at either Day 0 or Day 8, demonstrating that none of the treatments are antimicrobial. However, ACCS (II), AMP cells (III) and AMP cells+ACCS (IV) were all able to accelerated wound healing as compared to contaminated control (V) and UCM (I). The finding that all treatment groups can shift the healing curve to the left even when the wound is infected represents a significant improvement over currently available treatments.

The acute contaminated wounds were tested for breaking strength on Day 22 (Robson, et al: The effect of cytokine growth factors on the prevention of acute wound failure. Wound Rep Regen 12: 38-43, 2004. Franz, et al: Fascial incisions heal faster than skin: A new model for abdominal wall repair. Surgery 129: 203-208, 2001.). In the AMP cell and AMP cell+ACCS treated groups, there was a statistically significant (=p<0.05) increase in breaking strength when the results of two experiments were added together (13.5N each) as compared to UCM (10.5N) and ACCS alone (10N). As Day 22 is late in the wound healing time course, it is hypothesized that if breaking strength is tested earlier in the wound healing process, the difference between treated and untreated will be even greater.

Similar experiments as those described above for an acute contaminated wound model were performed using a chronic contaminated wound model (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.). Neither ACCS, AMP cells, nor AMP cells+ACCS had a significant impact on bacterial load at any of the days tested (Days 0, 8, 10), demonstrating again that none of the treatments are antimicrobial. Furthermore, ACCS (II), AMP cell (III), AMP cells+ACCS (IV) are able to accelerate wound healing significantly as compared to UCM (I) and contaminated control (VI). To achieve a 50% open wound, contaminated control took 18 days, whereas ACCS, AMP cells and ACCS+AMP cells achieved this by day about day 10-11. This shift of 6 days represents a significant improvement in healing rates than those achievable by currently available therapies.

Example 12

Evaluation of Accelerated Wound Strength and Prevention of Acute Wound Failure

One object of the invention is to decrease wound failure in surgical and traumatic injuries by treating these acute wounds with ACCS from AMP cells. The focus is muscle, fascial and skin wound healing in vivo following surgical injury. Wound fibroblasts are isolated to measure the effect of soluble mediators derived from AMP cells on repair fibroblast function in vitro.

Art-accepted animal models for evaluating wound strength and wound failure (Robson, et al: The effect of cytokine growth factors on the prevention of acute wound failure. Wound Rep Regen 12: 38-43, 2004. Franz, et al: Fascial incisions heal faster than skin: A new model for abdominal wall repair. Surgery 129: 203-208, 2001) were used in experiments to assess whether or not ACCS could increased wound strength and decrease wound failure.

The animals were randomly assigned into one of 12 Groups. In Experimental Designs 1 and 2, each of the three animal models (Sham laparotomy, Healing laparotomy and Hernia) were treated with four experimental conditions of ACCS containing the humoral products of AMP cells. (No treatment, Control AMP cell media (0% conditioned), 50% ACCS and 100% ACCS). 100 IU of media is delivered to the site of the laparotomy myofascial and skin incisions prior to wounding.

Results: The application of ACCS resulted in a statistically significant increase in breaking strength (=p<0.05) (16.7N) at Day 7 as compared to PBS (8N) and UCM (10.5N) in this animal model of wound failure. In addition, in this same animal model, the addition of ACCS resulted in a statistically significant increase in tensile strength (=p<0.05) ($0.34N/mm^2$) at Day 7 as compared to PBS ($0.21N/mm^2$) and UCM ($0.23N/mm^2$). These data indicate that ACCS is capable of increasing wound strength in this model.

Results obtained in the incisional hernia model: In the treatment group in which the incisions were "primed" with 100 µl ACCS only 25% of the animals formed incisional hernias, as compared to PBS or UCM (control groups) in which 100% of the animals developed incisional hernias. Furthermore, when the hernias were removed and their size measured, the ACCS treated group had an average hernia size that was ⅛ the size of the PBS treated controls and ¹⁄₁₂ the size of UCM controls. In addition, In the ACCS treated incision, there is no visible indication of the incisional wound, whereas in the UCM treated incision, there is an obvious visible suture line. A histological section through the surgical site in both an UCM treated and the ACCS treated animal reveals that in the ACCS treated specimen, there is thick, organized fascia (F), an organized and intact rectus muscle (RM) and a well healed peritoneum (P). These features are not evident in the UCM treated specimen. Taken together, these data clearly demonstrate that the application of ACCS prior to incisional injury can increase wound strength, decrease or prevent wound failure as evidenced by both reduced rate of hernia formation and hernia size, and accelerate wound healing.

Histology: Histological analyses of provisional matrix structure, fibroblast migration, inflammatory response and wound angiogenesis is used to compare the groups using H&E and trichrome staining of samples are collected from laparotomy wounds or incisional hernias from rats. The density of wound collagen formation is measured using antibodies specific for rat collagen types I and III (Chemicon International, Inc., Temecula, Calif.). Cellular infiltration into the wounds at each time-point is measured as the mean cell number from three high-powered fields by a blinded observer using a microscope. In addition, histological specimens are digitized using a UMAX Astra 1200S scanner and analyzed using the computer software application Adobe PhotoShop version 5.0. Differences in cellularity and intensity of collagen staining are compared using the Students t test (SigmaStat, Jandel).

Example 13

Use of AMP Cells, ACCS, Cell Lysates, and Cell Products for Rapid Early Wound Closure of Thermal Injuries Outcome and rehabilitation of thermal injuries rely on early burn wound excision and rapid wound closure. The speed of wound closure with a serviceable integument or integument substitute is the key to an improvement in survival. Providing novel approaches that will facilitate early, rapid wound closure, while minimizing long-term scarring, is an object of the present invention.

Established in vivo animal models were used to evaluate the use of AMP cells and ACCS for early, rapid wound closure of partial-thickness and full-thickness burns.

It is theorized that AMP cells can differentiate into mesodermal and ectodermal cells. Thus, it may be possible that use of such cells will provide early and permanent closure of the burn wound. Since presently, the prolonged time the wound is in the inflammatory phase is the known variable leading to proliferative scarring, it is expected that early, permanent closure of the burn wound would result in decreased scarring and, thus, increased function.

Three animal models of partial-thickness and full-thickness thermal injuries were used (DelBecarro, et al: The use of specific thromboxane inhibitors to preserve the dermal microcirculation after burning. Surgery 87: 137-141, 1980. Robson, et al: Increasing dermal perfusion after burning by decreasing thromboxane production. J Trauma 20: 722-725, 1980. Polo, et al: An in vivo model of human proliferative scar. J Surg Res 74: 187-195, 1998.). The three models are different because the first mimics partial-thickness healing by epithelialization in approximately three weeks while the second and third mimic full-thickness healing by contraction and epithelialization and can remain unhealed for up to eight weeks. The difference in the last two full-thickness wounds is the host. One group is a normal rat with an intact immune system, while the other is an athymic "nude" rat which is devoid of T-lymphocytes.

Partial-thickness wound results: Healing of partial-thickness (second degree) scald burns in guinea pigs is was accelerated using topical application of ACCS and/or topical application of AMP cells. Combining ACCS and AMP cells resulted in the greatest acceleration of burn wound healing.

Full thickness wound results: The rate of wound healing was accelerated in all of the treated groups (III, IV, and V) as compared to the two control groups (no treatment group (I) and UCM treated group (II)).

Example 14

Bone Differentiation Assays with AMP Cells

This initial series of alkaline-phosphatase (ALP) activity staining suggests differentiation of AMP cells towards an osteogenic lineage under the influence of both BMP2 and osteogenic supplement (OS) media. The experiment began at passage three, with AMP cells seeded below the ideal density. In general, cells cultured in osteogenic supplement (OS) assumed a flattened morphology and spread to create confluent layers on the flask surface.

Positive staining for ALP activity was observed as early as day three in AMP cells cultured in OS media, independent of BMP2 concentration. No ALP activity was observed in cultures supplemented only with BMP2 within three days. By day seven, the number of cells expressing ALP increased in all cultures under OS. Under OS and at high (100-200 ng/ml) BMP2 doses, the intensity of ALP staining declined indicating down-regulation of ALP at this time (expected). By day seven, ALP activity was seen in cells cultured in basal AMP cell media supplemented with BMP2. In particular, a large number of cells supplemented only with 200 ng/ml BMP2 showed strong ALP activity at day seven. By day ten, ALP expression was no longer evident in populations cultured with both OS media supplemented with higher (50-200 ng/ml) concentrations of BMP2. Presumably, ALP activity has decreased as the cells progress towards osteogenic lineage (this is the expected outcome). ALP staining can still be seen in OS media with lower concentrations of BMP2. At day ten, cells cultured without OS appear unhealthy and sparse, for reasons that are not clear. These data indicate that AMP cells cultured in an osteogenic supplement media exhibit markers associated with osteogenic differentiation.

Example 15

Ability of AMP Cells to Promote Complete Regeneration of Deep Wounds

Experiments are designed to promote complete regeneration of deep wounds through re-creating the all of the necessary tissues including bone, muscle, cartilage, skin, and neural tissue. Initially, in vitro experiments are designed to determine if AMP cells can differentiate into all of the cells of interest. AMP cells will be cultured as previously described. Mesenchymal stem cells (Cambrex, Rutherford, N.J.) will be used as a control for differentiation experiments. MSC's will be seeded at 5,000-6,000 cells per $cm^2$ and cultured in Mesenchymal Stem Cell Growth Medium (MSGM, Cambrex, Rutherford, N.J.).

Osteogenic: Once cells are confluent, growth media will be changed (DMEM, 10% FBS, 1% pen/strep) to osteogenic differentiation media (Shi, Y. Y., et al., (2005) *Plast Reconstr Surg* 116, 1686-96.) (DMEM, 10% FBS, 1% pen/strep, 250 uM ascorbate-2-phosphate, 10 mM beta-glycerophosphate, 2.5 uM retinoic acid). Osteogenic differentiation media will be changed every 2-3 days. Alkaline phosphatase activity of adipose-derived mesenchymal cells will be evaluated in duplicate wells after 7 days of culture. Alkaline phosphatase staining will be performed using the Alkaline Phosphatase Staining Kit (Sigma) following the manufacturer's recommendations. Experiments will be performed in triplicate. Von Kossa staining will be performed in duplicate wells to assess the ability of cells to mineralize the extracellular matrix and form bone nodules. Staining will be performed on cells after 21 days of culture in duplicate wells in differentiation media conditions. Cells will be fixed in neutral buffered formalin for 30 minutes, incubated with 1% aqueous silver nitrate for 15 minutes under ultraviolet light, stained with 5% sodium thiosulfate for 2 minutes, and finally counterstained with 1% Safranin O for 10 minutes. In addition, calcium concentration in the extracellular matrix will be determined via a biochemical calorimetric assay using the Calcium Reagent Set (Biotron Diagnostics, Hemet, Calif.) in duplicate wells. Experiments will be performed in triplicate.

Adipogenic: AMP cells and MSC will be cultured in adipogenic differentiation media (Shi, Y. Y., et al., (2005) *Plast Reconstr Surg* 116, 1686-96.) for 3 days (DMEM, 10% FBS, 1% pen/strep, 10 ug/ml insulin, 1 uM dexamethasone, 0.5 mM methylxanthine, 200 uM indomethacin), then change to adipocyte maintenance media for 2 more days (DMEM, 10% FBS, 1% pen/strep, 1 ug/ml insulin). Oil Red O staining will be performed to assess for adipogenic differentiation in duplicate wells (as indicated by the presence of intracellular lipid-filled droplets) after 5 days of culture in adipogenic media. Cells will be fixed in 10% neutral buffered formalin for 30 minutes and then incubated in 60% Oil Red O solution for 30 minutes at 37° C. Experiments will be performed in triplicate.

Chondrogenic: AMP cells and MSC will be cultured in standard non differentiation conditions and then collected and resuspended at $1 \times 10^7$ cells/ml concentration. Ten μl droplets will then be placed onto a culture dish and allowed to adhere to substratum at 37° C. for 2 hours. Then chondrogenic media (Malladi, P., et al., (2006) *Am J Physiol Cell Physiol* 290, C1139-46.) will be added carefully around cell aggregates (DMEM, 1% FBS, 1% pen/strep, 37.5 ug/ml ascorbate-2-phosphate, ITS premix (BD Biosciences), 10 ng/ml TGF-B1 (Research Diagnostics, Inc., Flanders, N.J.). Micromasses will be fixed in 4% paraformaldehyde with 4% sucrose for 15 minutes, embedded with Optimal Cutting Temperature (O.C.T.) compound. Ten μm cryosections will be mounted on slides and stained by hematoxylin and eosin and alcain blue. Immunohistochemistry will be performed as follows. Sections will be blocked at room temperature for 30 minutes and incubated with primary antibody at 4° C. overnight (anti-collagen II, Santa Cruz Biotechnology, Santa Cruz, Calif.). Followed by secondary antibody (Vector Labs, Burlingame, Calif.) incubation, 8 sections will be labeled with ABC reagent (Vector Labs, Burlingame, Calif.) for 10 minutes at room temperature. DAB (Vector Labs, Burlingame, Calif.) was applied to each section and hematoxylin will be used for counterstaining.

Skeletal myogenic: AMP cells and MSC will be cultured as previously described. Skeletal myogenic differentiation will be induced by culturing cells in myogenic medium (Gang, E. J., et al., (2004) *Stem Cells* 22, 617-24.) (culture medium supplemented with 5% horse serum, 0.1 μM dexamethasone, and 50 μM hydrocortisone) for up to 6 weeks. Myogenic differentiation will analyzed by FACS for MyoD1, myogenin, and myosin heavy chain (MyHC). For FACS, cells will be detached and stained sequentially with primary antibodies (human-anti MyoD and anti-myogenin antibodies; Becton Dickinson) and FITC-conjugated secondary antibodies (FITC-rat anti-human IgG1; Becton Dickinson). Cells will be fixed with 2% formaldehyde until analysis with FACS. For detection of an intracellular protein MyHC, cells were permeabilized with cold methanol/PBS for 2 minutes at −20° C. before staining with primary mouse anti-myosin (fast, Sigma) and FITC-conjugated secondary antibody.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for accelerating wound healing of a treated burn wound as compared to the healing rate of a non-treated burn wound in a patient in need thereof comprising treating the burn wound by topically administering to the patient's burn wound about $0.25$-$1.0 \times 10^6$ cultured amnion-derived epithelial cells, wherein the cultured amnion-derived epithelial cells are made by the method comprising the steps of a) obtaining a placenta and isolating an amnion from the placenta, b) enzymatically releasing amnion-derived epithelial cells from the amnion,
c) collecting the released amnion-derived epithelial cells, and
d) culturing the collected amnion-derived epithelial cells of step (c) in basal culture medium that is supplemented with human serum albumin and recombinant human EGF.

2. The method of claim 1 wherein the basal medium is IMDM.

3. The method of claim 2 wherein the IMDM is supplemented with 0.5% human serum albumin.

4. The method of claim 1 wherein the recombinant human EGF is at a concentration of 10 ng/mL of culture medium.

5. The method of claim 1 wherein the amnion-derived epithelial cells, the basal medium, and all medium supplements are free of xeno-contamination.

6. The method of claim 1 wherein the treatment increases tensile strength and breaking strength of the healing treated burn wound as compared to the tensile strength and breaking strength in a healing non-treated burn wound.

7. The method of claim 1 wherein the treatment reduces fibrosis and collagen contraction in a healing treated burn wound as compared to the fibrosis and collagen contraction in a healing non-treated burn wound.

* * * * *

UNITED STATES PATENT AND TRADEMARK OFFICE
CERTIFICATE OF CORRECTION

PATENT NO. : 8,871,198 B2
APPLICATION NO. : 11/724094
DATED : October 28, 2014
INVENTOR(S) : Charlotte A. Emig, Catherine J. Trunpower and Vivienne S. Marshall Page 1 of 1

It is certified that error appears in the above-identified patent and that said Letters Patent is hereby corrected as shown below:

In the Specification

In the Statement Regarding Federally Sponsored Research or Development in Column 1, Line 21, delete the words "may have" and insert the word --has--.

Signed and Sealed this
Eighth Day of May, 2018

Andrei Iancu
*Director of the United States Patent and Trademark Office*